United States Patent [19]

Mark et al.

[11] Patent Number: 4,959,314

[45] Date of Patent: * Sep. 25, 1990

[54] CYSTEINE-DEPLETED MUTEINS OF BIOLOGICALLY ACTIVE PROTEINS

[75] Inventors: David F. Mark, Danville; Leo S. Lin, Fremont; Shi-da Yu Lu, Cupertino, all of Calif.

[73] Assignee: Cetus Corporation, Emeryville, Calif.

[ * ] Notice: The portion of the term of this patent subsequent to May 21, 2002 has been disclaimed.

[21] Appl. No.: 698,939

[22] Filed: Feb. 7, 1985

Related U.S. Application Data

[63] Continuation-in-part of Ser. No. 564,224, Dec. 20, 1983, Pat. No. 4,518,584, which is a continuation-in-part of Ser. No. 486,162, Apr. 15, 1983, abandoned, which is a continuation-in-part of Ser. No. 435,154, Oct. 19, 1982, abandoned. Also continuation-in-part of Ser. No. 698,939, Feb. 7, 1985, Pat. No. 4,959,314, which is a continuation-in-part of Ser. No. 670,360, is a continuation-in-part of Ser. No. 661,026, Oct. 15, 1984, abandoned.

[51] Int. Cl.⁵ .................... C12P 21/00; C12P 19/34; C12P 21/22

[52] U.S. Cl. .................... 435/69.1; 530/350; 530/351; 530/324; 530/333; 435/172.3; 435/320; 435/252.3; 435/252.33; 435/91; 536/27; 514/2; 514/8; 514/12; 424/85.2; 424/85.6

[58] Field of Search ...... 435/68, 172.3, 253, 435/317, 69.1, 320, 252.3, 252.33; 530/324, 333, 350, 351, 828; 935/10, 27, 67, 73; 514/2, 8, 12; 536/27; 424/85.2, 85.6

[56] References Cited

U.S. PATENT DOCUMENTS

| | | | |
|---|---|---|---|
| 4,518,584 | 5/1985 | Mark et al. | 424/85 |
| 4,816,566 | 3/1989 | DeChiara et al. | 435/69.1 |

OTHER PUBLICATIONS

Itakura et al., *Science*, vol. 198, pp. 1056–1063, Dec. 9, 1977, Expression in *Escherichia coli* of a Chemically Synthesized Gene for the Lormone Somatostatr.

Zolter et al. *Methods in Enzymology*, vol. 100, pp. 468–500, 1983, "Oligonocteotide–Directed Mutagenesis of DNA Fragments Cloned Into M13 Vectors".

*Primary Examiner*—Robin L. Teskin
*Attorney, Agent, or Firm*—Albert P. Halluin; Jane R. McLaughlin; Kate H. Murashige

[57] ABSTRACT

Muteins of biologically active proteins such as IFN-β and IL-2 in which cysteine residues that are not essential to biological activity have been deleted or replaced with other amino acids to eliminate sites for intermolecular crosslinking or incorrect intramolecular disulfide bridge formation. These muteins are made via bacterial expression of mutant genes that encode the muteins that have been synthesized from the genes for the parent proteins by oligonucleotide-directed mutagenesis.

22 Claims, 19 Drawing Sheets

```
                    5                  10                 15                 20
    MetSerTyrAsnLeu LeuGlyPheLeuGln ArgSerSerAsnPhe GlnCysGlnLysLeu
                   25                 30                 35                 40
    LeuTrpGlnLeuAsn GlyArgLeuGluTyr CysLeuLysAspArg MetAsnPheAspIle
                   45                 50                 55                 60
    ProGluIleLys    GlnLeuGlnGlnPhe GlnLysGluAspAla AlaLeuThrIleTyr
                   65                 70                 75                 80
    GluMetLeuGlnAsn IlePheAlaIlePhe ArgGlnAspSerSer SerThrGlyTrpAsn
                   85                 90                 95                100
    GluThrIleValGlu AsnLeuLeuAlaAsn ValTyrHisGlnIle AsnHisLeuLysThr
                  105                110                115                120
    ValLeuGluGluLys LeuGluLysGluAsp PheThrArgGlyLys LeuMetSerSerLeu
                  125                130                135                140
    HisLeuLysArgTyr TyrGlyArgIleLeu HisTyrLeuLysAla LysGluTyrSerHis
                  145                150                155                160
    CysAlaTrpThrIle ValArgValGluIle LeuAgAsnPheTyr  PheIleAsnArgLeu
                  165                170                175                180
    ThrGlyTyrLeuArg Asn---
```

FIG. 1

IFN-B CYS TO SER CHANGE AT AMINO ACID 17

```
1                                                              17
ATG AGC TAC AAC TTG CTT GGA TTC CTA CAA AGA AGC AGC AAT TTT CAG AGT  CAG AAG CTC
met ser tyr asn leu leu gly phe leu gln arg ser ser asn phe gln ser  gln lys leu 61
CTG TGG CAA TTG AAT GGG AGG CTT GAA TAT TGC CTC AAG GAC AGG ATG AAC TTT GAC ATC
leu trp gln leu asn gly arg leu glu tyr cys leu lys asp arg met asn phe asp ile 121
CCT GAG GAG ATT AAG CAG CTG CAG CAG TTC CAG AAG GAG GAC GCC GCA TTG ACC ATC TAT
pro glu glu ile lys gln leu gln gln phe gln lys glu asp ala ala leu thr ile tyr 181
GAG ATG CTC CAG AAC ATC TTT GCT ATT TTC AGA CAA GAT TCA TCT AGC ACT GGC TGG AAT
glu met leu gln asn ile phe ala ile phe arg gln asp ser ser ser thr gly trp asn 241
GAG ACT ATT GTT GAG AAC CTC CTG GCT AAT GTC TAT CAT CAG ATA AAC CAT CTG AAG ACA
glu thr ile val glu asn leu leu ala asn val tyr his gln ile asn his leu lys thr 301
GTC CTG GAA GAA AAA CTG GAG AAA GAA GAT TTC ACC AGG GGA AAA CTC ATG AGC AGT CTG
val leu glu glu lys leu glu lys glu asp phe thr arg gly lys leu met ser ser leu 361
CAC CTG AAA AGA TAT TAT GGG AGG ATT CTG CAT TAC CTG AAG GCC AAG GAG TAC AGT CAC
his leu lys arg tyr tyr gly arg ile leu his tyr leu lys ala lys glu tyr ser his 421
TGT GCC TGG ACC ATA GTC AGA GTG GAA ATC CTA AGG AAC TTT TAC TTC ATT AAC AGA CTT
cys ala trp thr ile val arg val glu ile leu arg asn phe tyr phe ile asn arg leu 481
ACA GGT TAC CTC CGA AAC TGA AGA TC
thr gly tyr leu arg asn ***
```

FIG. 10

```
         10         20         30         40         50         60
ATGCCTACTT CAAGTTCTAC AAAGAAAACA CAGCTACAAC TGGAGCATTT ACTGCTGGAT
         70         80         90        100        110        120
TTACAGATGA TTTTGAATGG AATTAATAAT TACAAGAATC CCAAACTCAC CAGGATGCTC
        130        140        150        160        170        180
ACATTTAAGT TTTACATGCC CAAGAAGGCC ACAGAACTGA AACATCTTCA GTGTCTAGAA
        190        200        210        220        230        240
GAAGAACTCA AACCTCTGGA GGAAGTGCTA AATTTAGCTC AAAGCAAAAA CTTTCACTTA
        250        260        270        280        290        300
AGACCCAGGG ACTTAATCAG CAATATCAAC GTAATAGTTC TGGAACTAAA GGGATCTGAA
        310        320        330        340        350        360
ACAACATTCA TGTGTGAATA TGCTGATGAG ACAGCAACCA TTGTAGAATT TCTGAACAGA
        370        380        390        400        410        420
TGGATTACCT TTTCTCAGAG CATCATCTCA ACACTGACTT GA
```

FIG. 15a

```
                   5             10             15             20
      MetProThrSerSer SerThrLysLysThr GlnLeuGlnLeuGlu HisLeuLeuLeuAsp
                  25             30             35             40
      LeuGlnMetIleLeu AsnGlyIleAsnAsn TyrLysAsnProLys LeuThrArgMetLeu
                  45             50             55             60
      ThrPheLysPheTyr MetProLysLysAla ThrGluLeuLysHis LeuGlnCysLeuGlu
                  65             70             75             80
      GluGluLeuLysPro LeuGluGluValLeu AsnLeuAlaGlnSer LysAsnPheHisLeu
                  85             90             95            100
      ArgProArgAspLeu IleSerAsnIleAsn ValIleValLeuGlu LeuLysGlySerGlu
                 105            110            115            120
      ThrThrPheMetCys GluTyrAlaAspGlu ThrAlaThrIleVal GluPheLeuAsnArg
                 125            130            135            140
      TrpIleThrPheSer GlnSerIleIleSer ThrLeuThr---
```

```
         610        620        630        640        650        660        670        680        690       700
GCCATCAAGAGCCCCTGCCAGAGGAGACCCAGAGGGGCTGAGGCCAAGCCCTGGTATGAGCCCATCTATCTGGGAGGGGTCTTCCAGCTGGAGAAGGT
AlaIleLysSerProCysGlnArgGluThrProGluGlyAlaGluAlaLysProTrpTyrGluProIleTyrLeuGlyGlyValPheGlnLeuGluLysGly
                   100                                                                      110                                                  120

710        720        730        740        750        760        770        780        790       800
GACCGACTCAGCGCTGAGATCAATCGGCCCGACTATCTCGACTTTGCCGAGTCTGGGCAGTCTACTTGGGATCATTGCCCTGTGAGGAGGACGAACAT
AspArgLeuSerAlaGluIleAsnArgProAspTyrLeuAspPheAlaGluSerGlyGlnValTyrPheGlyIleIleAlaLeu
130                                                                      140                                                          150

810        820        830        840        850        860        870        880        890       900
CCAACCTTCCCAAAACGCCTCCCCTGCCCCAATCCCTTTATTACCCCCTCAGACACCCTCAACCTCTCTGGCTCAAAAGAGAATTGGGGGCTTAG 910        920        930        940        950        960        970        980        990      1000
GGTCGGAACCCAAGCTTAGAACTTTAAGCAACAAGACCACCACTTCGAAACTGGGATTCAGGAATGTGTGGCCCTGCACAGTGAAGTGCTGGCAACCACT 1010       1020       1030       1040       1050       1060       1070       1080       1090      1100
AAGAATTCAAACTGGGCCTCCAGAACTCACTGGGCCTACAGCTTTGATCCCTGACATCTGGAATCTGGAGACCAGGAGCCTTTGGTTCTGGCCAGAA 1110       1120       1130       1140       1150       1160       1170       1180       1190      1200
TGCTGCAGGACTTGAGAAGACCTCACCTAGAAAATTGACACAAGTGGACCTTAGGCACTTGTGATTATTATTATTTATTATTACAGACTTCCTGAGACACGGAGCC 1210       1220       1230       1240       1250       1260       1270       1280       1290      1300
CAGCCCTCCCATGGAGCCAGCTCCCCAGCTCCCTCTATTTATGTTTGCACTTGTTGATTATTATTATTATTATTATTATTACAGATGAATGTATTTATT 1310       1320       1330       1340       1350       1360       1370       1380       1390      1400
TGGGAGACCGGGGTATCCTGGGGACCCAATGTAGGAGCTGCCTTGGCTCAGACATGTTTCCGTGAAAACGGAGGCTGAACAATAGGCTGTTCCCATGT 1410       1420       1430       1440       1450       1460       1470       1480       1490      1500
AGCCCCCTGGCCTCTGTGCCTTCTGTGCCTTCTGTTTTTGATTATGTTTTTAAAATATTATCTGATTAAGTTGTCTAAACAATGCTGATTGGTGACCAACTGTCACTCAT 1510       1520       1530       1540       1550       1560       1570       1580       1590      1600
TGCTGAGGCCTCTGCCTCCCCAGGAGTTGTGTCTGTAATCGGCCTATTCAGTGGGCGAGAAATAAAGGTTGCTTAGGAAAGAA
```

```
          10         20         30         40         50         60
 ATGGTCAGAT CATCTTCTCG AACCCCGAGT GACAAGCCTG TAGCCCATGT TGTAGCAAAC
          70         80         90        100        110        120
 CCTCAAGCTG AGGGGCAGCT CCAGTGGCTG AACCGCCGGG CCAATGCCCT CCTGGCCAAT
         130        140        150        160        170        180
 GGCGTGGAGC TGAGAGATAA CCAGCTGGTG GTGCCATCAG AGGGCCTGTA CCTCATCTAC
         190        200        210        220        230        240
 TCCCAGGTCC TCTTCAAGGG CCAAGGCAGC CCGAGCACCC ATGTGCTCCT CACCCACACC
         250        260        270        280        290        300
 ATCAGCCGCA TCGCCGTCTC CTACCAGACC AAGGTCAACC TCCTCTCTGC CATCAAGAGC
         310        320        330        340        350        360
 CCCTGCCAGA GGGAGACCCC AGAGGGGCT GAGGCCAAGC CCTGGTATGA GCCCATCTAT
         370        380        390        400        410        420
 CTGGGAGGGG TCTTCCAGCT GGAGAAGGGT GACCGACTCA GCGCTGAGAT CAATCGGCCC
         430        440        450        460        470        480
 GACTATCTCG ACTTTGCCGA GTCTGGGCAG GTCTACTTTG GGATCATTGC CCTGTGAGGA
         490        500        510        520        530        540
 GGACGAACAT CCAACCTTCC CAAACGCCTC CCCTGCCCCA ATCCCTTTAT TACCCCCTCC
         550        560        570        580        590        600
 TTCAGACACC CTCAACCTCT TCTGGCTCAA AAAGAGAATT GGGGGCTTAG GGTCGGAACC
         610        620        630        640        650        660
 CAAGCTTAGA ACTTTAAGCA ACAAGACCAC CACTTCGAAA CCTGGGATTC AGGAATGTGT
         670        680        690        700        710        720
 GGCCTGCACA GTGAAGTGCT GGCAACCACT AAGAATTCAA ACTGGGCCT CCAGAACTCA
         730        740        750        760        770        780
 CTGGGGCCTA CAGCTTTGAT CCCTGACATC TGGAATCTGG AGACCAGGGA GCCTTTGGTT
         790        800        810        820        830        840
 CTGGCCAGAA TGCTGCAGGA CTTGAGAAGA CCTCACCTAG AAATTGACAC AAGTGGACCT
         850        860        870        880        890        900
 TAGGCCTTCC TCTCTCCAGA TGTTTCCAGA CTTCCTTGAG ACACGGAGCC CAGCCCTCCC
         910        920        930        940        950        960
 CATGGAGCCA GCTCCCTCTA TTTATGTTTG CACTTGTGAT TATTTATTAT TTATTTATTA
         970        980        990       1000       1010       1020
 TTTATTTATT TACAGATGAA TGTATTTATT TGGGAGACCG GGGTATCCTG GGGGACCCAA
        1030       1040       1050       1060       1070       1080
 TGTAGGAGCT GCCTTGGCTC AGACATGTTT TCCGTGAAAA CGGAGGCTGA ACAATAGGCT
        1090       1100       1110       1120       1130       1140
 GTTCCCATGT AGCCCCCTGG CCTCTGTGCC TTCTTTTGAT TATGTTTTTT AAAATATTAT
        1150       1160       1170       1180       1190       1200
 CTGATTAAGT TGTCTAAACA ATGCTGATTT GGTGACCAAC TGTCACTCAT TGCTGAGGCC
        1210       1220       1230       1240       1250       1260
 TCTGCTCCCC AGGGAGTTGT GTCTGTAATC GGCCTACTAT TCAGTGGCGA GAAATAAAGG
        1270       1280       1290       1300       1310       1320
 TTGCTTAGGA AAGAA
```

FIG. 20a

```
                           5              10              15              20
          MetValArgSerSer  SerArgThrProSer AspLysProValAla HisValValAlaAsn
                          25              30              35              40
          ProGlnAlaGluGly  GlnLeuGlnTrpLeu AsnArgArgAlaAsn AlaLeuLeuAlaAsn
                          45              50              55              60
          GlyValGluLeuArg  AspAsnGlnLeuVal ValProSerGluGly LeuTyrLeuIleTyr
                          65              70              75              80
          SerGlnValLeuPhe  LysGlyGlnGlySer ProSerThrHisVal LeuLeuThrHisThr
                          85              90              95             100
          IleSerArgIleAla  ValSerTyrGlnThr LysValAsnLeuLeu SerAlaIleLysSer
                         105             110             115             120
          ProCysGlnArgGlu  ThrProGluGlyAla GluAlaLysProTrp TyrGluProIleTyr
                         125             130             135             140
          LeuGlyGlyValPhe  GlnLeuGluLysGly AspArgLeuSerAla GluIleAsnArgPro
                         145             150             155             160
          AspTyrLeuAspPhe  AlaGluSerGlyGln ValTyrPheGlyIle IleAlaLeu---
          $
```

FIG. 20b

CYSTEINE-DEPLETED MUTEINS OF BIOLOGICALLY ACTIVE PROTEINS

CROSS-REFERENCE TO RELATED APPLICATION

This application is a continuation-in-part of U.S. Ser. No. 564,224, filed Dec. 20, 1983 now U.S. Pat. No. 4,518,584 which is a continuation-in-part of U.S. Ser. No. 486,162, now abandoned filed Apr. 15, 1983, which is a continuation-in-part of U.S Ser. No. 435,154 filed Oct. 19, 1982, now abandoned. It is also a continuation-in-part of U.S. Ser. No. 698,939 filed Feb. 7, 1985, now U.S. Pat. No. 4,959,314 which is a continuation-in-part of pending U.S. Ser. No. 670,360, filed Nov. 9, 1984, which is a continuation-in-part of U.S. Ser. No. 661,026, filed Oct. 15, 1984, now abandoned.

TECHNICAL FIELD

This invention is in the general area of recombinant DNA technology. More specifically it relates to mutationally altered biologically active proteins that differ from their parent analogs by one or more substitutions/deletions of cysteine residues.

BACKGROUND ART

Biologically active proteins that are microbially produced via recombinant DNA (rDNA) technology may contain cysteine residues that are nonessential to their activity but are free to form undesirable intermolecular or intramolecular links. One such protein is microbially produced human beta interferon (IFN-$\beta$). In the course of the preparation of IFN-$\beta$ by rDNA techniques, it has been observed that dimers and oligomers of microbially produced IFN-$\beta$ are formed in *E. coli* extracts containing high concentrations of IFN-$\beta$. This multimer formation renders purification and separation of IFN-$\beta$ very laborious and time-consuming and necessitates several additional steps in purification and isolation procedures such as reducing the protein during purification and reoxidizing it to restore it to its original conformation, thereby increasing the possibility of incorrect disulfide bond formation. Furthermore, microbially produced IFN-$\beta$ has also been found to exhibit consistently low specific activity due perhaps to the formation of multimers or of random intramolecular disulfide bridges. It would be desirable, therefore, to be able to alter microbially produced biologically active proteins such as IFN-$\beta$ in a manner that does not affect their activity adversely but reduces or eliminates their ability to form intermolecular crosslinks or intramolecular bonds that cause the protein to adopt an undesirable tertiary structure (e.g., a conformation that reduces the activity of the protein).

The present invention is directed to producing by directed mutagenesis techniques mutationally altered biologically active proteins (such proteins are called "muteins", *Glossary of Genetics and Cytogenetics*, 4th Ed, p 381, Springer-Verlag (1976)) that retain the activity of their parent analogs but lack the ability to form intermolecular links or undesirable intramolecular disulfide bonds. In this regard Shepard, H. M., et al, *Nature* (1981) 294:563–565 describe a mutein of IFN-$\beta$ in which the cysteine at position 141 of its amino acid sequence (there are three cysteines in native human IFN-$\beta$ at positions 17, 31, and 141, *Gene* (1980) 10:11–15 and *Nature* (1980) 285:542–547) is replaced by tyrosine. This mutein was made by bacterial expression of a hybrid gene constructed from a partial IFN-$\beta$ cDNA clone having a G→A transition at nucleotide 485 of the IFN-$\beta$ gene. The mutein lacked the biological activity of native IFN-$\beta$ leading the authors to conclude that the replaced cysteine was essential to activity.

Directed mutagenesis techniques are well known and have been reviewed by Lather, R. F. and Lecoq, J. P. in *Genetic Engineering* Academic Press (1983) pp 31–50. Oligonucleotide-directed mutagenesis is specifically reviewed by Smith, M. and Gillam, S. in *Genetic Engineering: Principles and Methods*, Plenum Press (1981) 3:1–32.

DISCLOSURE OF THE INVENTION

One aspect of the invention is a synthetic mutein of a biologically active protein which protein has at least one cysteine residue that is free to form a disulfide link and is nonessential to said biological activity, said mutein having at least one of said cysteine residues deleted or replaced by another amino acid.

Another aspect of the invention relates to synthetic structural genes having DNA sequences that have been specifically designed ("designer genes") to encode the above described synthetic muteins. Subaspects of this aspect are expression vectors that include such structural designer genes, host cells or organisms transformed with such vectors, and processes for making the synthetic mutein by culturing such transformants or their progeny and recovering the mutein from the culture. In the case of muteins that have therapeutic utility, therapeutic compositions that contain therapeutically effective amounts of the muteins and therapeutic methods are other aspects of the invention.

Another aspect of the invention is a method of preventing a protein having one or more cysteine residues that is free to form an undesirable disulfide link from forming such a link comprising mutationally altering the protein by deleting the cysteine residue(s) or replacing them with other amino acids.

Still another aspect of the invention is a method for making the above described synthetic structural gene by oligonucleotide-directed mutagenesis comprising the following steps:

(a) hybridizing single-stranded DNA comprising a strand of a structural gene that encodes the parent protein with a mutant oligonucleotide primer that is complementary to a region of the strand that includes the codon for the cysteine to be deleted or replaced or the antisense triplet paired with the codon, as the case may be, except for a mismatch with that codon or antisense triplet, as the case may be, that defines a deletion of the codon or a triplet that encodes said other amino acid;

(b) extending the primer with DNA polymerase to form a mutational heteroduplex; and (c) replicating the mutational heteroduplex.

The mutant oligonucleotide primers used in this process are another aspect of the invention.

BRIEF DESCRIPTION OF THE DRAWINGS

FIG. 1 is a diagram of the amino acid sequence of IFN-$\beta$.

FIG. 10 shows the coding DNA sequence for the mutein IFN-$\beta_{ser17}$ with the corresponding amino acid sequence therefor.

FIGS. 15a and 15b show, respectively, the nucleotide sequence of the coding strand of the clone pLW46 and the corresponding amino acid sequence of the IL-2 mutein designated IL-2$_{ser125}$.

FIG. 18 shows the complete nucleotide sequence of pE4, and the deduced amino acid sequence.

FIGS. 20a and 20b show the complete nucleotide sequence of the insert encoding the mature TNF protein in pAW731, and the deduced amino acid sequence, respectively.

MODES FOR CARRYING OUT THE INVENTION

Figure 2:
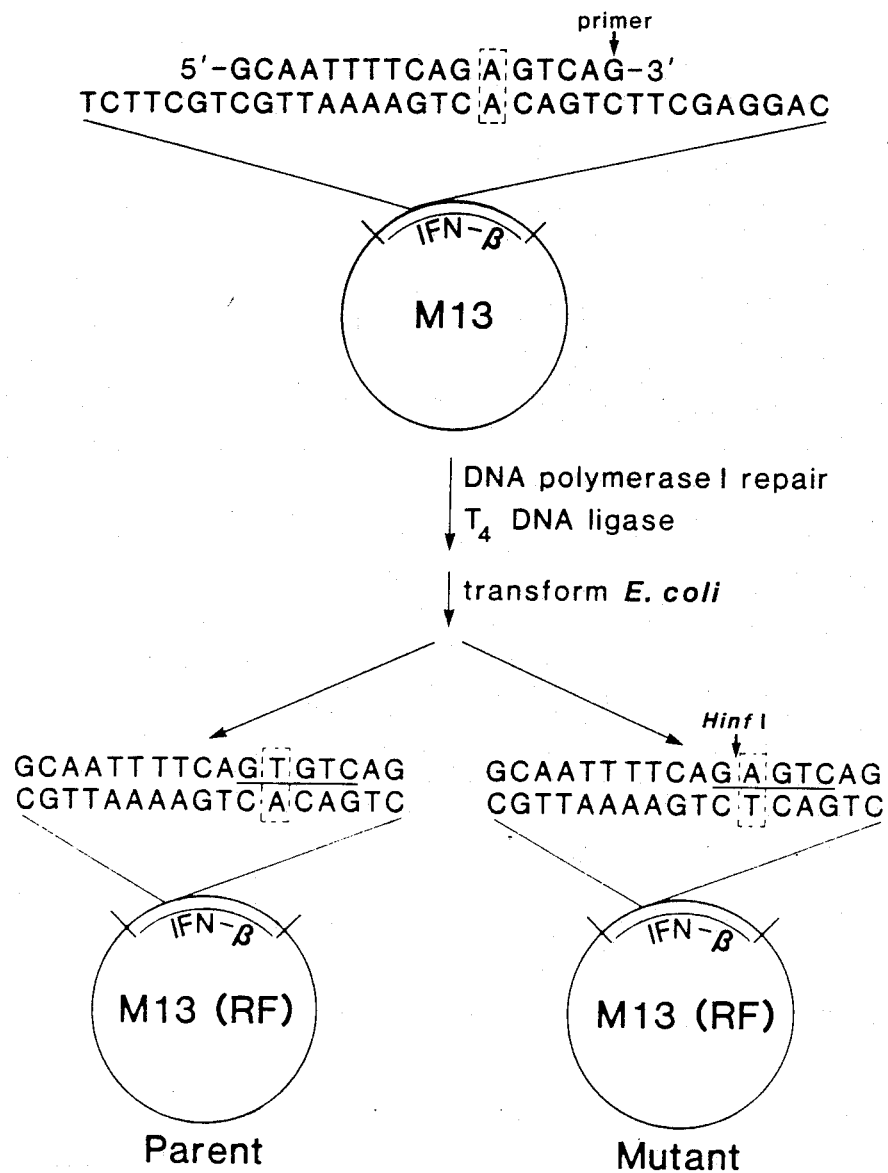
FIG. 2 is a schematic illustration showing the preparation of a mutant IFN-$\beta$ gene by oligonucleotide-directed mutagenesis.

The present invention provides muteins of biologically active proteins in which cysteine residues that are not essential to biological activity have been deliberately deleted or replaced with other amino acids to eliminate sites for intermolecular crosslinking or incorrect intramolecular disulfide bond formation; mutant genes coding for such muteins; and means for making such muteins.

Proteins that may be mutationally altered according to this invention may be identified from available information regarding the cysteine content of biologically active proteins and the roles played by the cysteine residues with respect to activity and tertiary structure. For proteins for which such information is not available in the literature this information may be determined by systematically altering each of the cysteine residues of the protein by the procedures described herein and testing the biological activity of the resulting muteins and their proclivity to form undesirable intermolecular or intramolecular disulfide bonds. Accordingly, while the invention is specifically described and exemplified below as regards muteins of IFN-$\beta$, IL-2 and tumor necrosis factor (TNF) it will be appreciated that the following teachings apply to any other biologically active protein that contains a functionally nonessential cysteine residue that makes the protein susceptible to undesirable disulfide bond formation. Examples of proteins other than IFN-$\beta$, TNF, and IL-2 that are candidates for mutational alteration according to the invention are lymphotoxin, colony stimulating factor-1 and IFN-$\alpha$1. Candidate proteins sometimes have an odd number of cysteine residues.

The cysteine residues are either deleted or replaced with amino acids which do not affect the biological activity of the resulting mutein. Appropriate amino acid residues are selected from the group consisting of serine, threonine, glycine, alanine valine, leucine, isoleucine, histidine, tyrosine, phenylalanine, tryptophan, and methionine. Preferred among this group are the residues of serine, threonine, alanine, and valine. Particularly preferred is replacement by a serine residue.

In the case of IFN-$\beta$ it has been reported in the literature and that both the glycosylated and unglycosylated IFNs show qualitatively similar specific activities and that, therefore, the glycosyl moieties are not involved in and do not contribute to the biological activity of IFN-$\beta$. However, bacterially produced IFN-$\beta$ which is unglycosylated consistently exhibits quantitatively lower specific activity than native IFN-$\beta$ which is glycosylated. IFN-$\beta$ is known to have three cysteine residues at positions 17, 31 and 141. Cysteine 141 has been demonstrated by Shepard, et al, supra, to be essential for biological activity. In IFN-$\alpha$, which contains four cysteine residues, there are two intramolecular —S—S— bonds: one between cys 29 and cys 138 and another between cys 1 and cys 98. Based on the homology between IFN-$\beta$ and IFN-$\alpha$s cys 141 of IFN-$\beta$ could be involved in an intramolecular —S—S— bond with cys 31, leaving cys 17 free to form intermolecular crosslinks. By either deleting cys 17 or substituting it by a different amino acid, one can determine whether cys 17 is essential to biological activity, and its role in —SS— bond formation. If cys 17 is not essential for the biological activity of the protein, the resulting cys 17-deleted or cys 17-substituted protein might exhibit specific activity close to that of native IFN-$\beta$ and would possibly also facilitate isolation and purification of the protein.

By the use of the oligonucleotide-directed mutagenesis procedure with a synthetic oligonucleotide primer that is complementary to the region of the IFN-$\beta$ gene at the codon for cys 17 but which contains single or multiple base changes in that codon, a designer gene may be produced that results in cys 17 being replaced with any other amino acid of choice. When deletion is desired the oligonucleotide primer lacks the codon for cys 17. Conversion of cys 17 to neutral amino acids such as glycine, valine, alanine, leucine, isoleucine, tyrosine, phenylalanine, histidine, tryptophan, serine, threonine and methionine is the preferred approach. Serine and threonine are the most preferred replacements because of their chemical analogy to cysteine. When the cysteine is deleted, the mature mutein is one amino acid shorter th n the native parent protein or the microbially produced IFN-$\beta$.

Human IL-2 is reported to have three cysteine residues located at positions 58, 105, and 125 of the protein. As in the case of IFN-$\beta$, IL-2 is in an aggregated oligomeric form when isolated from bacterial cells and has to be reduced with reducing agents in order to obtain a good yield from bacterial extracts. In addition, the purified reduced IL-2 protein is unstable and readily reoxidized upon storage to an oligomeric inactive form. The presence of three cysteines means that upon reoxidation, the protein may randomly form one of three possible intramolecular disulfide bridges, with only one of those being the correct bridge as found in the native molecule. Since the disulfide structure of the native IL-2 protein is not known, it is possible to use the present invention to create mutations at codons 58, 105 and 125 of the IL-2 gene and identify which cysteine residues are necessary for activity and therefore most likely to be involved in native disulfide bridge formation. In the same vein, the cysteine residue that is not necessary for activity can be modified so as to prevent the formation of incorrect intramolecular disulfide bridges and minimize the chance of intermolecular disulfide bridges by removal or replacement of the free cysteine residue.

Human TNF is a 157 amino acid Protein containing two cysteine residues, one at Position 69 and the other at position 101. TNF was first deported by Carswell et al. *Proc Natl Acad Sci* (USA) (1975) 72:3666: and has been shown to be cytotoxic selectively to neoplastic cells. TNF has been purified from cell culture, by Matthews, et al *Brit J Cancer* (1981) 44:418 (from mononuclear phagocytes derived from BCG-injected rabbits) and by Mannel et al, *Infect Immun* (1980) 30:523, *ibid* (1981) 33:156 from cultures of macrophage enriched peritoneal exudate cells from BCG-infected mice. The sequence encoding TNF produced by the human promyelocytic leukemia cell line (HL-60, ATCC #CCL240) has been cloned and expressed in *E coli* and has been shown to have the sequence set forth in FIG. 18.

As will be shown below, neither of the cysteine residues in the TNF sequence appears to be involved in disulfide linkages, and either may be replaced or deleted according to the method of the invention to obtain a stable and biologically active mutein.

The size of the oligonucleotide primer is determined by the requirement for stable hybridization of the primer to the region of the gene in which the mutation is to be induced, and by the limitations of the currently available methods for synthesizing oligonucleotides. The factors to be considered in designing oligonucleotides for use in oligonucleotide-directed mutagenesis (e.g., overall size, size of portions flanking the mutation site) are described by Smith, M. and Gillam S., supra. In general the overall length of the oligonucleotide will be such as to optimize stable, unique hybridization at the mutation site with the 5' and 3' extensions from the mutation site being of sufficient size to avoid editing of the mutation by the exonuclease activity of the DNA polymerase. Oligonucleotides used for mutagenesis in accordance with the present invention usually contain from about 12 to about 24 bases, preferably from about 14 to about 20 bases and still more preferably from about 15 to about 18 bases. They will usually contain at least about three bases 3' of the altered or missing codon.

The method for preparing the modified IFN-$\beta$ gene broadly involves inducing a site-specific mutagenesis in the IFN-$\beta$ gene at codon 17 (TGT) using a synthetic nucleotide primer which omits the codon or alters it so that it codes for another amino acid. When threonine replaces the cysteine and the primer is hybridized to the antisense strand of the IFN-$\beta$ gene, the preferred nucleotide primer is GCAATTTTCACTCAG (underlining denotes the altered codon). When it is desirable to delete cysteine, the preferred primer is AGCAATTTTCAGCAGAAGCTCCTG, which omits the TGT codon for cys. When cysteine is replaced by serine, a 17-nucleotide primer, GCAATTTTCAGAGTCAG, which includes an AGT codon for serine is the primer of choice. The T->A transition of the first base in the cys 17 codon results in changing cysteine to serine. It must be recognized that when deletions are introduced, the proper reading frame for the DNA sequence must be maintained for expression of the desired protein.

The primer is hybridized to single-stranded phage such as M13, fd, or $\phi$X174 into which a strand of the IFN-$\beta$ gene has been cloned. It will be appreciated that the phage may carry either the sense strand or antisense strand of the gene. When the phage carries the antisense strand the primer is identical to the region of the sense strand that contains the codon to be mutated except for a mismatch with that codon that defines a deletion of the codon or a triplet that codes for another amino acid. When the phage carries the sense strand the primer is complementary to the region of the sense strand that contains the codon to be mutated except for an appropriate mismatch in the triplet that is paired with the codon to be deleted. Conditions that may be used in the hybridization are described by Smith, M. and Gillam, S., supra. The temperature will usually range between about 0° C. and 70° C., more usually about 10° C. to 50° C. After the hybridization, the primer is extended on the phage DNA by reaction with DNA polymerase I, T$_4$ DNA polymerase, reverse transcriptase or other suitable DNA polymerase. The resulting dsDNA is converted to closed circular dsDNA by treatment with a DNA ligase such as T$_4$ DNA ligase. DNA molecules containing single-stranded regions may be destroyed by S1 endonuclease treatment.

Oligonucleolide-directed mutagenesis may be similarly employed to make a mutant IL-2 gene that encodes a mutein having IL-2 activity but having cys 125 changed to serine 125. The preferred oligonucleotide primer used in making this mutant IL-2 gene when the phage carries the sense strand of the gene is GATGATGCTCTGAGAAAAGGTAATC. This oligonucleotide has a C→G change at the middle base on the triplet that is paired with codon 125 of the IL-2 gene.

Similarly, oligonucleotide directed mutagenesis is employed to obtain a mutant TNF gene that encodes a mutein having TNF activity, but with cys$_{69}$ changed to an alternate or deleted amino acid, and/or the cys$_{101}$ residue replaced or deleted. For the exemplified conversion of the cys$_{69}$ to ser$_{69}$, a preferred oligonucleotide primer is 5'-CATGGGTGCTCGGGCTGCCTT-3' This oligonucleotide has a T->A change in the triplet that is paired with codon 69 of the TNF gene. Similarly, cys$_{101}$ may be converted to ser$_{101}$ with a primer CAAGAGCCCCTCTCAGAGGGAG which contains a corresponding change at the triplet paired with the codon at 101, using ssM13 phage DNA containing the appropriate strand of the human TNF cDNA sequence.

The resulting mutational heteroduplex is then used to transform a competent host organism or cell. Replication of the heteroduplex by the host provides progeny from both strands. Following replication the mutant gene may be isolated from progeny of the mutant strand, inserted into an appropriate expression vector, and the vector used to transform a suitable host organism or cell. Preferred vectors are plasmids pBR322, pCR1, and variants thereof, synthetic vectors and the like. Suitable host organisms are *E. coli, Pseudomonas, Bacillus subtilis, Bacillus thuringiensis*, various strains of yeast, *Bacillus thermophilus*, animal cells such as mice, rat or Chinese hamster ovary (CHO) cells, plant cells, animal and plant hosts and the like. It must be recognized that when a host of choice is transformed with the vector, appropriate promoter-operator sequences are also introduced in order for the mutein to be expressed. Hosts may be prokaryotic or eukaryotic (processes for inserting DNA into eukaryotic cells are described in PCT applications nos US81/00239 and US81/00240 published 3 Sept. 1981). E. coli and CHO cells are the preferred hosts. The muteins obtained in accordance with the present invention may be glycosylated or unglycosylated depending on the glycosylation occurring in the native parent protein and the host organism used to produce the mutein. If desired, unglycosylated mutein obtained when E. coli or a Bacillus is host organism, may be optionally glycosylated in vitro by chemical, enzymatic and other types of modifications know in the art.

In the preferred embodiment of the subject invention respecting IFN-$\beta$, the cysteine residue at position 17 in the amino acid sequence of IFN-$\beta$, as shown in FIG. 1, is changed to serine by a T->A transition of the first base of codon 17 of the sense strand of the DNA sequence which codes for the mature IFN-$\beta$. The site-specific mutagenesis is induced using a synthetic 17-nucleotide primer GCAATTTTCAGAGTCAG which is identical to a seventeen nucleotide sequence on the sense strand of IFN-$\beta$ in the region of codon 17 except for a single base mismatch at the first base of codon 17. The mismatch is at nucleotide 12 in the primer. It must be recognized that the genetic code is degenerate and that many of the amino acids may be encoded by more than one codon. The base code for serine, for example, is six-way degenerate such that the codons, TCT, TCG, TCC, TCA, AGT, and ACG all code for serine. The AGT codon was chosen for the preferred embodiment for convenience. Similarly, threonine is encoded by any one of the codons ACT, ACA, ACC and ACG. It is intended that when one codon is specified for a particular amino acid, it includes all degenerate codons which encode that amino acid. The 17-mer is hybridized to single-stranded M13 phage DNA which carries the antisense strand of the IFN-$\beta$ gene. The oligonucleotide primer is then extended on the DNA using DNA polymerase I Klenow fragment and the resulting dsDNA is converted to closed circular DNA with T$_4$ ligase. Replication of the resulting mutational heteroduplex yields clones from the DNA strand containing the mismatch. Mutant clones may be identified and screened by the appearance or disappearance of specific restriction sites, antibiotic resistance or sensitivity, or by other methods known in the art. When cysteine is substituted with serine, the T->A transition, shown in FIG. 2, results in the creation of a new HinfI restriction site in the structural gene. The mutant clone is identified by using the oligonucleotide primer as a probe in a hybridization screening of the mutated phage plaques. The primer will have a single mismatch when hybridized to the parent but will have a perfect match when hybridized to the mutated phage DNA, as indicated in FIG. 2. Hybridization conditions can then be devised where the oligonucleotide primer will preferentially hybridize to the mutated DNA but not to the parent DNA The newly generated HinfI site also serves as a means of confirming the single base mutation in the IFN-$\beta$ gene.

The M13 phage DNA carrying the mutated gene is isolated and spliced into an appropriate expression vector, such as plasmid pTrp3, and E. coli strain MM294 is transformed with the vector. Suitable growth media for culturing the transformants and their progeny are known to those skilled in the art. The expressed mutein of IFN-$\beta$ is isolated, purified and characterized.

The following examples are presented to help in the better understanding of the subject invention and for purposes of illustration only. They are not to be construed as limiting the scope of the invention in any manner. Examples 1-11 describe the preparation of a mutein of IFN-$\beta$. Examples 12-20 describe the preparation of a mutein of IL-2. Examples 21-27 describe the preparation of a TNF mutein, and its assay.

EXAMPLE 1

Figure 3:
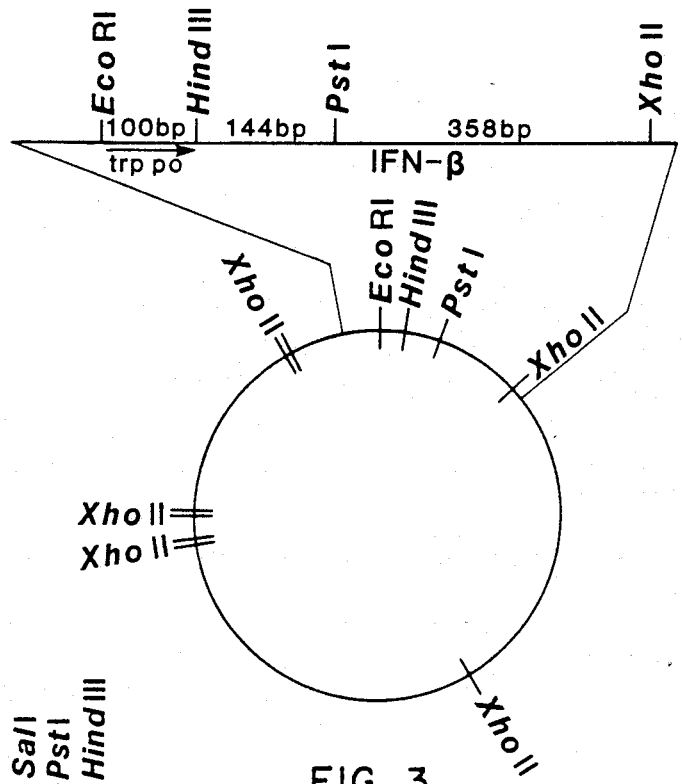
FIG. 3 shows a diagram of plasmid p$\beta$ltrp including the IFN-$\beta$ gene.
Figure 4:
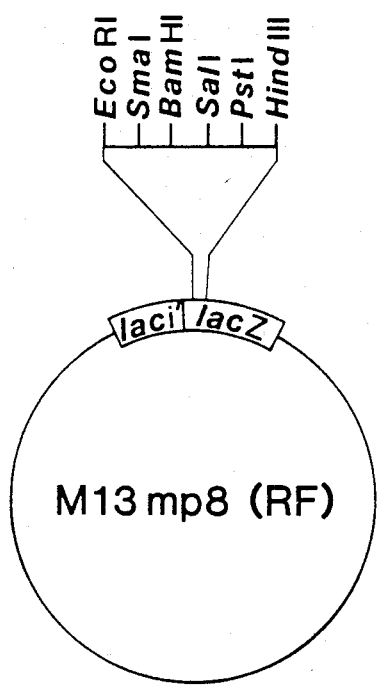
FIG. 4 is a diagram of the cloning vector M13mp8 phage.
Figure 5:
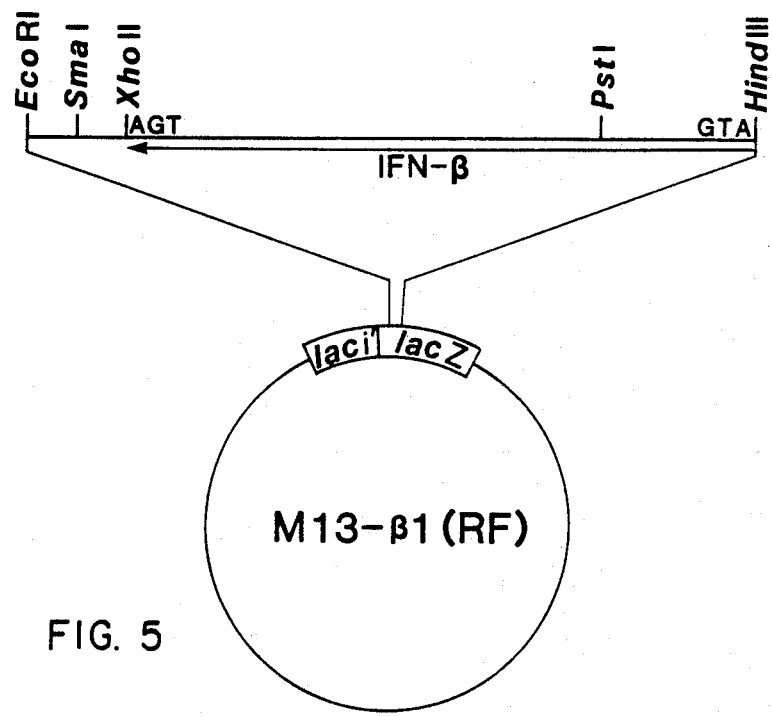
FIG. 5 shows the restriction map of clone M13-$\beta$1.

Cloning of the IFN-B Gene Into M13 Vector:

The use of M13 phage vector as a source of single-stranded DNA template has been demonstrated by G. F. Temple et al, *Nature* (1982) 296:537-540. Plasmid p$\beta$ltrp (FIG. 3) containing the IFN-$\beta$ gene under control of E. coli trp promoter, was digested with the restriction enzymes HindIII and XhoII. The M13mp8 (J. Messing, "Third Cleveland Symposium on Macromolecules: Recombinant DNA," Ed. A Walton, Elsevier Press, 143-153 (1981)) replicative form (RF) DNA (FIG. 4) was digested with restriction enzymes HindIII and BamHI, and mixed with the p$\beta$ltrp DNA which had previously been digested with HindIII and XhoII. The mixture was then ligated with T$_4$ DNA ligase and the ligated DNA transformed into competent cells of E. coli strain JM 103 and plated on Xgal indicator plates (J. Messing, et al, *Nucleic Acids Res* (1981) 9:309-321). Plaques containing recombinant phage (white plaques) were picked, inoculated into a fresh culture of JM 103 and minipreps of RF molecules prepared from the infected cells (H. D. Birnboim and J. Doly, *Nucleic Acid Res* (1979) 7:1513-1523). The RF molecules were digested with various restriction enzymes to identify the clones containing the IFN-$\beta$ insert. The restriction map of one such clone (M13-$\beta$1) is shown in FIG. 5. Single-stranded (ss) phage DNA was prepared from clone M13-$\beta$1 to serve as a template for site-specific mutagenesis using a synthetic oligonucleotide.

EXAMPLE 2

Site-Specific Mutagenesis;

Forty picomoles of the synthetic oligonucleotide GCAATTTTCAGAGTCAG (primer) was treated with T$_4$ kinase in the presence of 0.1 mM adenosine triphosphate (ATP), 50 mM hydroxymethylaminomethane hydrochloride (Tris-HCl) pH 8.0, 10 mM MgCl$_2$, 5 mM dithiothreitol (DTT) and 9 units of T$_4$ kinase, in 50 $\mu$l at 37° C. for 1 hr. The kinased primer (12 pmole) was hybridized to 5$\mu$g of ss M13-$\beta$1 DNA in 50$\mu$l of a mixture containing 50 mM NaCl, 10 mM Tris-HCl, pH 8.0, 10 mM MgCl$_{22}$ and 10 mM $\beta$-mercaptoethanol, by heating at 67° C. for 5 min and at 42° C. for 25 min. The annealed mixture was then chilled on ice and then added to 50 $\mu$l of a reaction mixture containing 0.5 mM each of deoxynucleoside triphosphate (dNTP), 80 mM Tris-HCl, pH 7.4, 8 mM MgCl$_{22}$, 100 mM NaCl, 9 units of DNA polymerase I, Klenow fragment, 0.5 mM ATP and 2 units of T$_4$ DNA ligase, incubated at 37° C. for 3 hr and at 25° C. for 2 hr. The reaction was then terminated by phenol extraction and ethanol precipitation. The DNA was dissolved in 10 mM Tris-HCl pH 8.0, 10 mM ethylenediaminetetraacetic acid (EDTA), 50% sucrose and 0.05% bromophenylblue and electrophoresed on 0.8% agarose gel in the presence of 2 $\mu$g/ml of ethidium bromide. The DNA bands corresponding to the RF forms of M13-$\beta$1 were eluted from gel slices by the perchlorate method (R. W. Davis, et al, "Advanced Bacterial Genetics", Cold Spring Harbor Laboratory, N.Y., p. 178-179 (1980)). The eluted DNA was used to transform competent JM 103 cells, grown overnight and ssDNA isolated from the culture supernatant. This ssDNA was used as a template in a second cycle of primer extension, the gel purified RF forms of the DNA were transformed into competent JM 103 cells, plated onto agar plates and incubated overnight to obtain phage plaques.

EXAMPLE 3

Site Specific Mutagenesis

The experiment of Example 2 above is repeated except that the synthetic oligonucleotide primer used is GCAATTTTCAGACTCAG to change codon 17 of the IFN-β gene from one that codes for cysteine to one that codes for threonine.

EXAMPLE 4

Site Specific Deletion

The experiment of Example 2 above is repeated except that the synthetic oligonucleotide primer used is AGCAATTTTCAGCAGAAGCTCCTG to delete codon 17 of the IFN-β gene.

EXAMPLE 5

Screening And Identification of Mutagenized Plaques

Plates containing mutated M13-β1 plaques (Example 1) as well as two plates containing unmutated M13-β1 phage plaques, were chilled to 4° C. and plaques from each plate transferred onto two nitrocellulose filter circles by layering a dry filter on the agar plate for 5 min for the first filter and 15 min for the second filter. The filters were then placed on thick filter papers soaked in 0.2 N NaOH, 1.5 M NaCl and 0.2% Triton X-100 for 5 min, and neutralized by layering onto filter papers soaked with 0.5 M Tris-HCl, pH 7.5 and 1.5 M NaCl for another 5 min. The filters were washed in a similar fashion twice on filters soaked in 2×SSC (standard saline citrate), dried and then baked in a vacuum oven at 80° C. for 2 hr. The duplicate filters were prehybridized at 55° C. for 4 hr with 10 ml per filter of DNA hybridization buffer (5×SSC) pH 7.0, 4×Denhardt's solution (polyvinylpyrrolidine, ficoll and bovine serum albumin, 1×=0.02% of each), 0.1% sodium dodecyl sulfate (SDS), 50 mM sodium phosphate buffer pH 7.0 and 100 μg/ml of denatured salmon sperm DNA. $^{32}$p-labeled probe was prepared by kinasing the oligonucleotide primer with $^{32}$p-labeled ATP. The filters were hybridized to $3.5 \times 10^5$ cpm/ml of $^{32}$p-labeled primer in 5 ml per filter of DNA hybridization buffer at 55° C. for 24 hr. The filters were washed at 55° C. for 30 min each in washing buffers containing 0.1% SDS and decreasing amounts of SSC. The filters were washed initially with buffer containing 2×SSC and the control filters containing unmutated M13-β1 plaques were checked for the presence of any radioactivity using a Geiger counter. The concentration of SSC was lowered stepwise and the filters washed until no detectable radioactivity remained on the control filters with the unmutated M13-β1 plaques. The lowest concentration of SSC used was 0.1×SSC. The filters were air dried and autoradiographed at −70° C. for 2-3 days. 480 plaques of mutated M13-β1 and 100 unmutated control plaques were screened with the kinased oligonucleotide probe. None of the control plaques hybridized with the probe while 5 mutated M13-β1 plaques hybridized with the probe.

Figure 6:
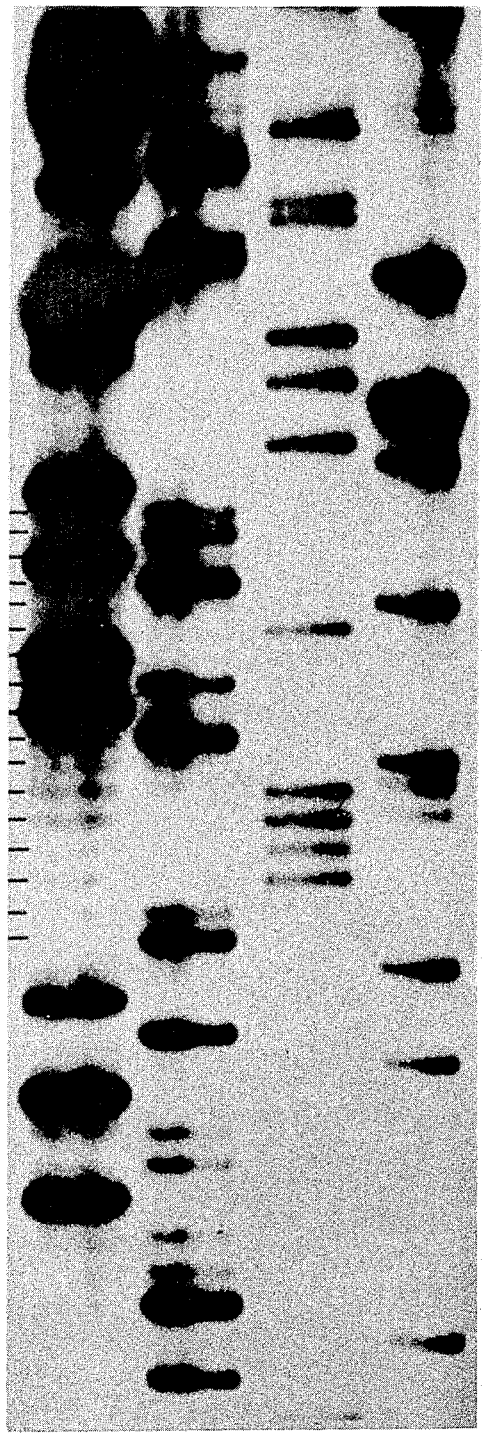
FIG. 6 shows the sequencing gel pattern of the mutant IFN-$\beta_{ser17}$ gene showing a single base change in the coding region.

One of the five mutated M13-β1 plaques (M13-SY2501) was picked and inoculated into a culture of JM 103. ssDNA was prepared from the supernatant and double-stranded (ds) DNA was prepared from the cell pellet. The ssDNA was used as a template for the dideoxy-sequencing of the clone using the M13 universal primer. The result of the sequence analysis is shown in FIG. 6, confirming that the TGT cys codon has been converted to an AGT ser codon.

EXAMPLE 6

Expression of Mutated IFN-β in E. coli

Figure 7:
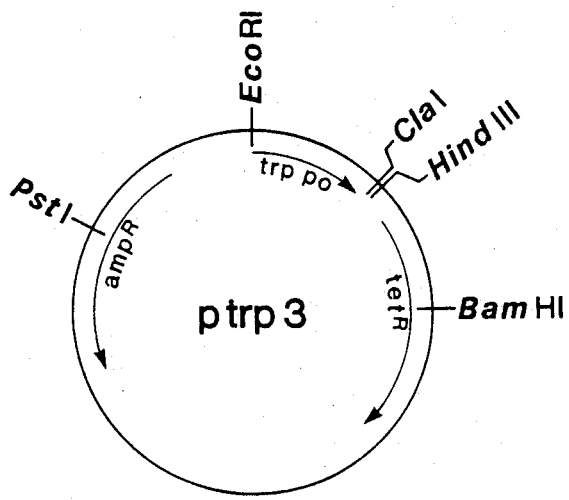
FIG. 7 is a diagram of the expression plasmid pTrp3.
Figures 8A, 8B:
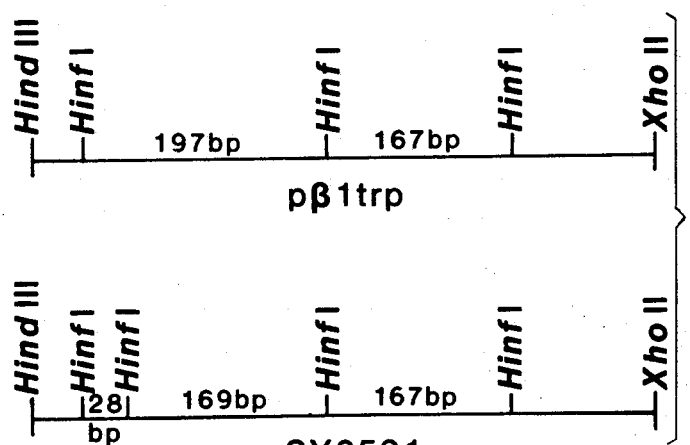
FIG. 8a shows the HinfI restriction pattern of clone pSY2501 and FIG. 8b shows the resulting two 169bp and 28bp fragments thereof.
Figure 9:
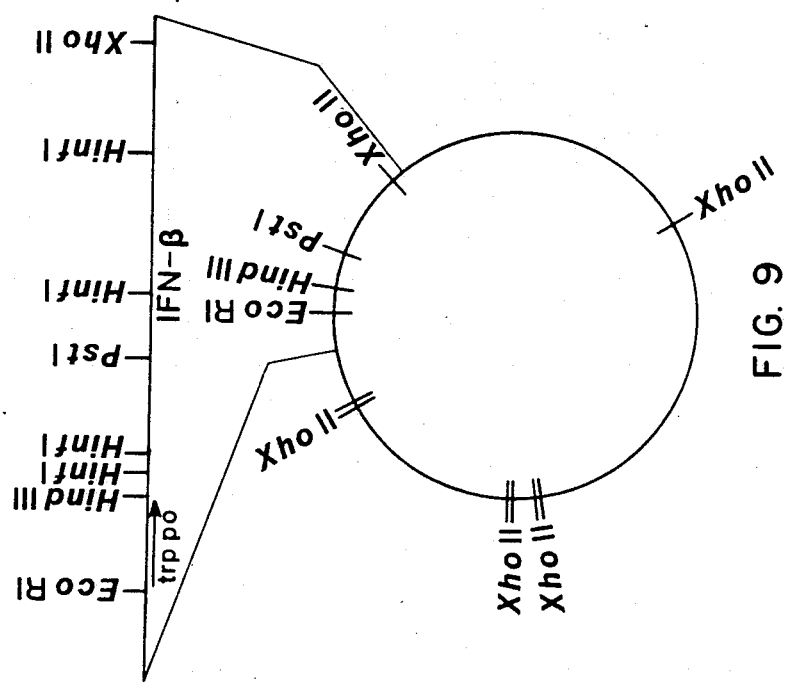
FIG. 9 is a restriction map of clone pSY2501.

RF DNA from M13-SY2501 was digested with restriction enzymes HindIII and XhoII and the 520 bp insert fragment purified on a 1% agarose gel. The plasmid pTrp3 containing the E. coli trp promoter (FIG. 7) was digested with the enzymes HindIII and BamHI, mixed with the purified M13-SY2501 DNA fragment, and ligated in the presence of T4 DNA ligase. The ligated DNA was transformed into E. coli strain MM294. Ampicillin resistant transformants were screened for sensitivity to the drug tetracycline. Plasmid DNA from five ampicillin resistant, tetracylcine sensitive clones were digested with HinfI to screen for the presence of the M13-SY2501 insert. FIG. 8a shows the HinfI restriction pattern of one of the clones (pSY2501), comparing it with the HinfI pattern of the original IFN-β clone, pβ1trp. As expected, there is an additional HinfI site in pSY2501, cleaving the 197 bp IFN-β internal fragment to a 169 bp fragment and a 28 bp fragment (FIG. 8b). A restriction map of the clone pSY2501 is shown in FIG. 9. The complete DNA sequence of the mutant IPN-β gene is shown in FIG. 10 together with the predicted amino acid sequence.

The plasmid designated as clone pSY2501 was deposited with the Agricultural Research Culture Collection (NRRL), Fermentation Laboratory, Northern Regional Research Center, Science and Education Administration, U.S. Department of Agriculture, 1815 North University Street, Peoria, Ill. 60604 on 30 Mar. 1983 and was assigned accession numbers CMCC No. 1533 and NRRL No. B-15356.

Cultures of pSY2501 and pβ1trp, which include progeny thereof, were grown up to an optical density (OD$_{600}$) of 1.0. Cell free extracts were prepared and the amount of IFN-β antiviral activity assayed on GM2767 cells in a microtiter assay. Extracts of clone pSY2501 exhibited three to ten times higher activity than pβ1trp (Table I), indicating that clone pSY2501 was either synthesizing more protein exhibiting IFN-β activity or that the protein made had a higher specific activity.

TABLE I

| EXTRACT | ANTIVIRAL ACTIVITY (U/ml) |
| --- | --- |
| pSY2501 | $6 \times 10^5$ |
| pβ1trp | $1 \times 10^5$ |
| ptrp3 (control) | 30 |

Figure 11:
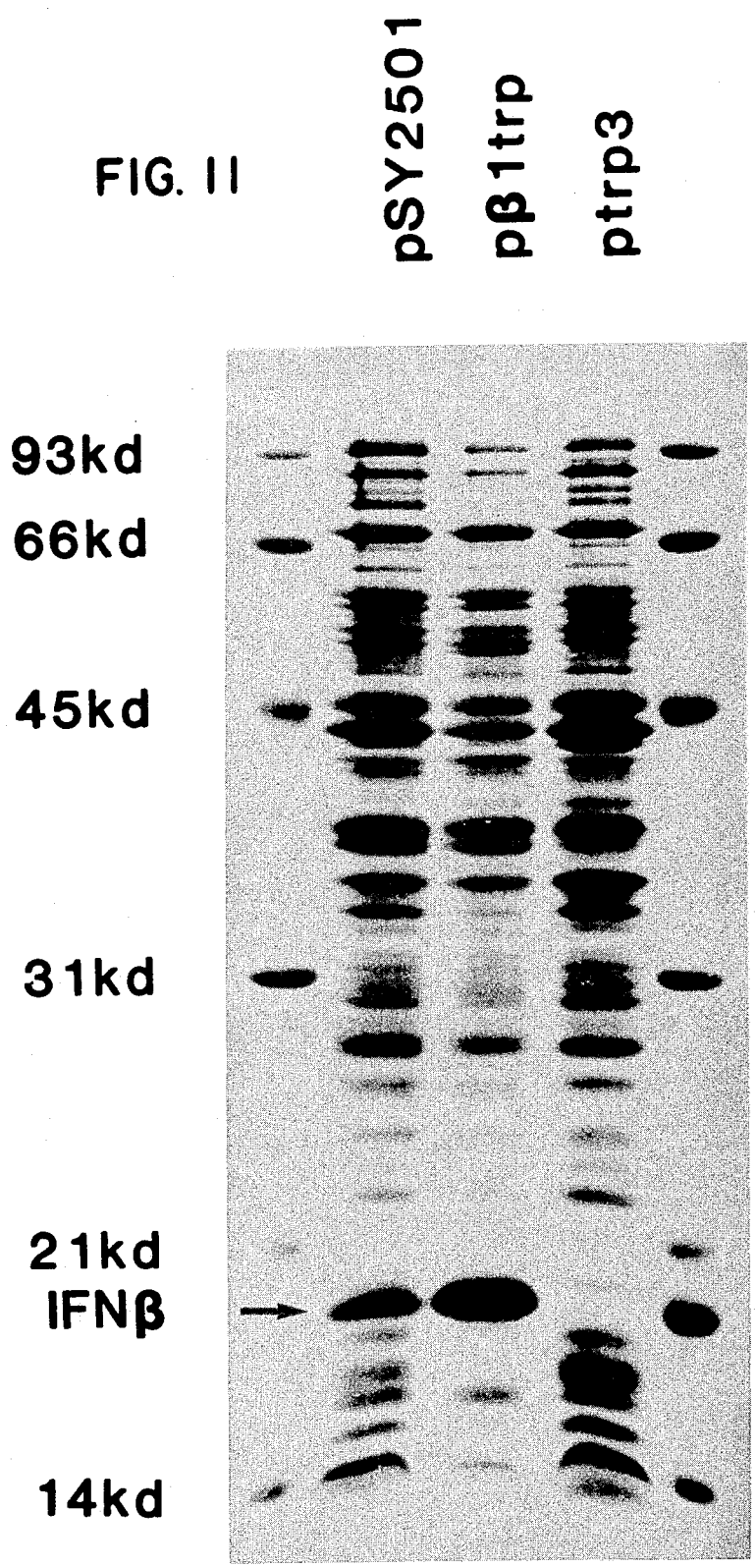
FIG. 11 shows the single 18,000 dalton protein band corresponding to IFN-$\beta_{ser17}$ in the extracts of clones pSY2501 and p$\beta$1trp.

In order to determine if clone pSY2501 was synthesizing several times more active protein, the extracts of both clones were electrophoresed on a SDS polyacrylamide gel together with a control extract and the gel stained with coomasie blue to visualize the proteins. As shown in FIG. 11, there was only one protein band corresponding to an apparent 18,000 dalton protein that was present in the extracts of clones pSY2501 and pβ1trp but not in the control extract of ptrp3. This protein, which has a molecular weight of about 20,000 daltons but shows a gel migration pattern of an 18,000 dalton protein was previously shown to be IFN-β by purification of this protein from extracts of pβltrp. Since there is less of this protein in extracts of pSY2501 than in extracts of pβltrp, the specific activity of the protein in extracts of clone pSY2501 was higher than that of clone pβ1trp.

EXAMPLE 7

The plasmid pSY2501 was transformed into a competent subvariant of *E. coli* strain MM294, designated MM294-1. A sample of the resulting transformant was deposited in the American Type Culture Collection 12301 Parklawn Drive, Rockville, Md. 20852 USA on 18 Nov. 1983; under ATCC number 39,517.

EXAMPLE 8

Production of IFN-$\beta_{ser17}$

IFN-$\beta_{ser17}$ was recovered from *E. coli* that had been transformed to produce IFN-$\beta_{ser17}$. The *E. coli* were grown in the following growth medium to an OD of 10–11 at 680 nm (dry wt 8.4 g/l).

| Ingredient | Concentration |
| --- | --- |
| $NH_4Cl$ | 20 mM |
| $K_2SO_4$ | 16.1 mM |
| $KH_2PO_4$ | 7.8 mM |
| $Na_2HPO_4$ | 12.2 mM |
| $MgSO_4.7H_2O$ | 3 mM |
| $Na_3$ citrite.$2H_2O$ | 1.5 mM |
| $MnSO_4.4H_2O$ | 30 μM |
| $ZnSO_4.7H_2O$ | 30 μM |
| $CuSO_4.5H_2O$ | 3 μM |
| L-tryptophan | 70 mg/l |
| $FeSO_4.7H_2O$ | 72 μM |
| thiamine.HCl | 20 mg/l |
| glucose | 40 g/l | pH control with $NH_4OH$

A 9.9 l (9.9 kg) harvest of the transformed *E. coli* was cooled to 20° C. and concentrated by passing the harvest through a cross-flow filter at an average pressure drop of ~110 kpa and steady-state filtrate flow rate of 260 ml/min until the filtrate weight was 8.8 kg. The concentrate (approximately one liter) was drained into a vessel and cooled to 15° C. The cells in the concentrate were then disrupted by passing the concentrate through a Manton-Gaulin homogenizer at 5° C., ~69,000 kpa. The homogenizer was washed with one liter phosphate buffered saline, pH 7.4 (PBS), and the wash was added to the disruptate to give a final volume of two liters. This volume was continuously centrifuged at 12000×g at a 50 ml/min flow rate. The solid was separated from the supernatant and resuspended in four liters PBS containing 2% by wt SDS. This suspension was stirred at room temperature for 15 min after which there was no visible suspended mater-The solution was then extracted with 2-butanol at a 1:1 2-butanol:solution volume ratio. The extraction was carried out in a liquid-liquid phase separator using a flow rate of 200 ml/min. The organic phase was then separated and evaporated to dryness to yield 21.3 g of protein. This was resuspended in distilled water at a 1:10 volume ratio.

The recovered product was assayed for human IFN-β activity using an assay based on protection against viral cytopathic effect (CPE). The assay was made in microtiter plates. Fifty μl of minimum essential medium were charged into each well and 25 μl of the sample was placed in the first well and 1:3 volume dilutions were made serially into the following wells. Virus (vesicular stomatitus), cell (human fibroblast line GM-2767), and reference IFN-β controls were included on each plate. The reference IFN-β used was 100 units per ml. The plates were then irradiated with UV light for 10 min. After irradiation 100 μl of the cell suspension ($1.2 \times 10^5$ cells/ml) was added to each well and the trays were incubated for 18–24 hr. A virus solution at one plaque-forming unit per cell was added to each well except the cell control. The trays were then incubated until the virus control showed 100% CPE. This normally occurred 18–24 hr after adding the virus solution. Assay results were interpreted in relation to the location of the 50% CPE well of the reference IFN-β control. From this point the titer of interferon for all samples on the plate was determined. The specific activity of the recovered product was determined to be $5 \times 10^7$ U/mg.

EXAMPLE 9

Acid Precipitation And Chromatographic Purification

The process of Example 8 was repeated except that after extraction and separation of the aqueous and organic phases and mixing of the organic phase with PBS at a volume ratio of 3:1 the pH of the mixture was lowered to about 5 by addition of glacial acetic acid. The resulting precipitate was separated by centrifugation at 10000–17000×g for 15 min and the pellet was redissolved in 10% w/v SDS, 10 mM DTT, 50 mM sodium acetate buffer, pH 5.5, and heated to 80° C. for 5 min.

The solution was then applied to a Brownlee RP-300, 10 μM, "Aquapore" column using a Beckman gradient system. Buffer A was 0.1% trifluoroacetic acid (TFA) in $H_2O$; buffer B was 0.1% TFA in acetonitrile. Detection was by ultraviolet absorbance at 280 nm. The solvent program was linear gradient of 0% buffer B to 100% buffer B in three hr. Fractions containing highest interferon activities were pooled and the specific activity of the pooled interferon preparation was determined to be $9.0 \times 10^7$ to $3.8 \times 10^8$ international units per mg protein, as compared to about $2 \times 10^8$ U/mg for native IFN-β.

EXAMPLE 10

Biochemical Characterization of IFN-βSer$_{17}$

Amino acid compositions were determined after 24–72 hr timed hydrolysis of 40 μg samples of IFN in 200 μl of 5.7 N HCl, 0.1% phenol, at 108° C. Proline and cysteine were determined in the same fashion after performic acid oxidation; in this case, phenol was omitted from the hydrolysis. Tryptophan was analyzed after 24 hr hydrolysis of 400 μl samples in 5.7 N HCl, 10% mercaptoacetic acid (no phenol). Analysis was performed on a Beckman 121MB amino acid analyzer using a single column of AA10 resin.

The amino acid composition calculated from representative 24-,48-, 72-hr acid hydrolyses of purified IFN-β Ser$_{17}$ agrees well with that predicted by the DNA sequence of the cloned IFN gene, minus the missing N-terminal methionine.

The amino acid sequence of the first 58 residues from the amino acid terminus of purified IFN was determined on a 0.7 mg sample in a Beckman 890C. sequanator with 0.1M Quadrol buffer. PTH amino acids were determined by reverse-phase HPLC on an Altex ultrasphere ODS column (4.6×250 mm) at 45° C. eluted at 1.3 min at 40% buffer B, and 8.4 min from 40–70% buffer B, where buffer A was 0.0115M sodium acetate, 5% tetrahydrofuran (THF), pH 5.11 and buffer B was 10% THF in acetonitrile.

The N-terminal amino acid sequence of IFN-β Ser$_{17}$ determined matches the expected sequence predicted from the DNA sequence, except for the absence of N-terminal methionine.

EXAMPLE 11

Alternative IFN-β$_{ser}$ Production and Purification Process

E.coli transformed with pSY2501 were grown in the following medium:

| Ingredient | Approximate Initial Concentration |
|---|---|
| Na$_3$ Citrate.2H$_2$O | 3 mM |
| KH$_2$PO$_4$ | 30 mM |
| (NH$_4$)$_2$SO$_4$ | 74 mM |
| MgSO$_4$.7H$_2$O | 3 mM |
| MnSO$_4$.H$_2$O | 46 μM |
| ZnSO$_4$.7H$_2$O | 46 μM |
| CuSO$_4$.5H$_2$O | 1–2 μM |
| L-tryptophan | 350 μM |
| FeSO$_4$.7H$_2$O | 74 μM |
| thiamine.HCl | 0.002% |
| glucose | 0.5% |

Dow Corning Antifoam polypropylene glycol, 25% solution, glucose, 50% solution, and KOH, 5N, were added on demand.

Temperature was maintained at 37±1° C., pH at 6.5±0.1 with NaOH, and dissolved oxygen at 30% of air saturation. Optical density and residual glucose measurements were taken at 14 hr and at approximately one hr intervals thereafter. Harvest was made when glucose consumption reached 40±6 g/l (OD at 680 nm = 10-11).

The harvested material was concentrated approximately 3-fold by circulating it through a microporous cross-flow filter under pressure. The concentrated cells were diafiltered against deionized water until the harvest material was concentrated 4-5 fold. The cells were then disrupted by passing them through a Manton-Gaulion homogenizer at ~4.1-5.5×10$^4$ kpa. After the initial pass SDS-sodium phosphate buffer was added to a final concentration of 2% SDS, 0.08M sodium phosphate and homogenization was continued for one hr. Solid DTT was then added to a final concentration of 50 mM and the homogenizate was heated to 90±5° C. for 10 min. The resulting cell suspension was extracted with 2-butanol at a 1:1 2-butanol:suspension volume ratio in a static mixer. The mixture was then centrifuged and the 2-butanol rich phase was collected.

The 2-butanol rich phase was mixed with 2.5 volumes of 0.1% SDS in PBS. Solid DTT was added to a final concentration of 2 mM. The pH of the mixture was adjusted to 6.2±0.1 with glacial acetic acid and this mixture was centrifuged. The resulting paste was collected and resuspended in PBS +10% SDS with pH adjustment to 8.5±0.1 using 1 N NaOH. Solid DTT was added to a final concentration of 100 mM and the suspension was heated to 90±5° C. for 10 min. The suspension was then cooled to ~25° C., the pH was adjusted to 5.5±0.1 with glacial acetic acid, and the solution was filtered.

The solution was then applied to a Sephacryl S-200 pre column and the fractions containing highest interferon activities were pooled and concentrated by ultrafiltration with a 10 Kdal molecular weight cutoff. The concentrate was oxidized by adding equimolar amounts of protein and iodosobenzoic acid into a reaction vessel containing 2 mM sodium pyrophosphate, 0.1% SDS and 1 mM EDTA. The pH was controlled during oxidation at 9.0±0.1 with 0.5 N NaOH and adjusted to 5.5±0.2 when oxidation was complete After oxidation the concentrate was again passed through the ultrafiltration unit with a 10 Kdal molecular weight cutoff.

The concentrate was applied to a main Sephacryl S-200 column and the fractions were analyzed by SDS-PAGE to determine those containing no high molecular weight contaminants. Those fractions were pooled and passed through the ultrafiltration unit. The filtered concentrate was then fractionated on a Sephadex G-75 column. SDS-PAGE analysis of the fractions was made to determine those containing no low or high molecular weight contaminants. Those fractions were pooled for desalting.

A Sephadex G-25 column equilibrated with 1 mM NaOH was loaded with the pooled fractions from the Sephadex G-75 column using distilled water adjusted to pH 10.8–11 with 50% NaOH. The purified product was collected as the void volume peak. This desalted, purified IFN-β mutein may be formulated in known manners for therapeutic administration.

Biological Testing of IFN-β$_{ser17}$

Antigenic Comparison

IFN-β$_{ser17}$ was compared antigenically to IFN-β produced from diploid fibroblasts using virus neutralizing tests A polyvalent antiserum to the diploid fibroblast IFN-β was prepared in rabbits. This antiserum blocked the antiviral activity of both the diploid fibroblast IFN-β and the IFN-β$_{ser17}$ in the virus neutralization tests, indicating the two proteins are indistinguishable antigenically.

Antiviral Activity

The purified IFN-β$_{ser17}$ was compared in its antiviral activity to naturally produced IFN-β. Inhibition of vesicular stomatitis virus replication in diploid foreskin fibroblast (HS27F) was indistinguishable from that of the natural molecule. Similarly, inhibition of herpes simplex virus type 1 in HS27F fibroblasts by the natural and mutant proteins were comparable.

Antiproliferative Activity

The antiproliferation activity of IFN-β$_{ser17}$ for continuous cell lines was compared with that of naturally produced IFN-β. T24 cells derived from a transitional cell carcinoma were treated with 200 units/ml of the proteins. Cell growth was inhibited significantly ($p<0.02$) by both proteins

Natural Killer (NK) Cell Stimulation

The ability of IFN-β$_{ser17}$ to stimulate NK cell (spontaneous cell mediated cytotoxicity) activity was tested. Ficoll-hypaque separated peripheral human mononuclear cells (PMC) or NK-enriched lymphocyte preparations (depleted of monocytes by plastic adherence and of OKT3-positive T cells by treatment with OKT3 antibody plus complement) were incubated overnight in growth medium containing various concentrations of IFN-β$_{ser17}$. $^{51}$Cr-labeled target cells were incubated with the effector cells (effector cell:target cell ratio=50:1) for 2-4 hours. NK cell cytoxicity was determined by measuring the amount of label released into the medium. The results of these tests are reported in Table I below.

TABLE I

| Target Cell | Effector Cells | NK Cell Cytotoxicity by Interferon (specific % $^{51}$Cr release ± SEM) IFN (units/ml) | | | | | |
|---|---|---|---|---|---|---|---|
| | | 0 | 10 | 30 | 100 | 300 | 1000 |
| T24 | PMC | 7.23 ± 5.1 | 23.1 ± 4.4 | 24.4 ± 1.1 | 34.1 ± 2.5 | 50.0 ± 2.0 | 40.4 ± 4.4 |
| Chang | PMC | 4.7 ± 0.5 | 7.2 ± 0.8 | 9.5 ± 1.7 | 15.9 ± 1.3 | 21.9 ± 1.4 | 26.9 ± 1.8 |
| Chang | NK Enr | 19.2 ± 4.6 | 39.4 ± 4.1 | ND | 54.2 ± 6.1 | ND | 41.7 ± 5.5 |
| K562 | NK Enr | 41.0 ± 4.6 | 48.4 ± 3.6 | ND | 62.2 ± 3.5 | ND | 63.2 ± 3.5 |

As shown the target cells were killed more effectively by the IFN-$\beta_{ser17}$-treated cells than by the untreated cells.

Clinical Trials

Phase I clinical trials to verify the safety of IFN-$\beta_{ser17}$ in humans have been initiated. These trials involve administering the protein to patients intramuscularly and intravenously at doses ranging between $1 \times 10^5$ units (1 µg of protein) to $400 \times 10^6$ units. In initial phase I clinical trials no unexpected adverse effects have occurred.

As indicated above, the, IFN-$\beta_{ser17}$ preparation exhibits specific activity levels very close to or better than that of native IFN-$\beta$. IFN-$\beta_{ser17}$ has no free sulfhydryl groups but indicates one —S—S— bond between the only remaining cysteines at positions 31 and 141. The protein does not readily form oligomers and appears to be substantially in the monomeric form. The IFN-$\beta_{ser17}$ obtained in accordance with this invention may be formulated either as a single product or mixtures of the various forms, into pharmaceutically acceptable preparations in inert, nontoxic, nonallergenic, physiologically compatible carrier media for clinical and therapeutic uses in cancer therapy or in conditions where interferon therapy is indicated and for viral infections such as herpes simplex virus I and II, hepatitis B virus, common cold viruses, and rhinovirus. Such media include but are not limited to distilled water, physiological saline, Ringer's solution, Hank's solution and the like. Other nontoxic stabilizing and solubilizing additives such as dextrose, HSA (human serum albumin) and the like may be optionally included. The therapeutic formulations may be administered orally or parenterally such as intravenous, intramuscular, intraperitoneal and subcutaneous administrations. Preparations of the modified IFN-( of the present invention may also be used for topical applications in appropriate media normally utilized for such purposes The IFN-B mutein may be administered either locally or systemically by itself or in combination or conjunction with other therapeutic agents such as cyclovir for prophylactic or therapeutic purposes The dose of mutein administered to human patients will depend on whether it is administered continuously (including intermittant) or as a bolus. The amounts administered continuously will typically be lower than the amounts administered as a bolus. The amount will usually be in the range of about $1 \times 10^5$ to $4 \times 10^8$ units, more usually about $1 \times 10^6$ to $1 \times 10^7$ units.

The principal advantages of the above described mutein of IFN-$\beta$ lie in the elimination of a free sulfhydryl group at position 17 in IFN-$\beta$, thereby forcing the protein to form correct disulfide links between cys 31 and cys 141 and to assume the conformation ostensibly required for full biological activity. The increased specific activity of the IFN-$\beta_{ser17}$ enables the use of smaller dosages in therapeutic uses. By deleting the cysteine at position 17 and eliminating the free —SH group, the IFN-$\beta_{ser17}$ protein does not form dimers and oligomers so readily as the microbially produced IFN-$\beta$. This facilitates purification of the protein and enhances its stability.

EXAMPLE 12

The nucleotide sequence for a cDNA clone coding for human IL-2, procedures for preparing IL-2 cDNA libraries, and screening same for IL-2 are described by Taniguchi, T., et al, *Nature* (1983) Vol 24, p 305 et seq.

cDNA libraries enriched in potential IL-2 cDNA clones were made from an IL-2 enriched mRNA fractions obtained from induced peripheral blood lymphocytes (PBL) and Jurkat cells by conventional procedures. The enrichment of the mRNA for IL-2 message was made by fractionating the mRNA and identifying the fraction having IL-2 mRNA activity by injecting the fractions in *Xenopus laevis* oocytes and assaying the oocyte lysates for IL-2 activity on HT-2 cells (J. Watson, *J Exp Med* (1979) 150:1570-1519 and S. Gillis et al, *J Immun* (1978) 120:2027-2032.)

EXAMPLE 13

Screening and Identification of IL-2 cDNA Clones

The IL-2 cDNA libraries were screened using the colony hybridization procedure. Each microtiter plate was replicated onto duplicate nitrocellulose filter papers (S & S type BA-85) and colonies were allowed to grow at 37° C. for 14-16 hr on L agar containing 50 µg/ml ampicillin. The colonies were lysed and DNA fixed to the filter by sequential treatment for 5 min with 500 mM NaOH, 1.5 M NaCl, washed twice for 5 min each time with 5× standard saline citrate (SSC). Filters were air dried and baked at 80° C. for 2 hr. The duplicate filters were pre-hybridized at 42° C. for 6-8 hr with 10 ml per filter of DNA hybridization buffer (50% formamide, 5×SSC, pH 7.0, 5×Denhardt's solution (polyvinylpyrrolidine, plus ficoll and bovine serum albumin; 1× =0.2% of each), 50 mM sodium phosphate buffer at pH 7.0, 0.2% SDS, 20 µg/ml Poly U, and 50 µg/ml denatured salmon sperm DNA.

A 32P-labeled 20-mer oligonucleotide probe was prepared based on the IL-2 gene sequence reported by Taniguchi, T., et al, supra. The nucleotide sequence of the probe was GTGGCCTTCTTGGGCATGTA.

The samples were hybridized at 42° C. for 24-36 hr with 5 ml/filter of DNA hybridization buffer containing the $^{32}$P cDNA probe. The filters were washed two times for 30 min each time at 50° C. with 2×SSC, 0.1% SDS, then washed twice with 1×SSC and 0.1% SDS at 50° C. for 90 min, air dried, and autoradiographed at −70° C. for 2 to 3 days. Positive clones were identified and rescreened with the probe. Full length clones were identified and confirmed by restriction enzyme mapping and comparison with the sequence of the IL-2 cDNA clone reported by Taniguchi, T., et al, supra.

EXAMPLE 14

Cloning of Il-2 Gene into M13 Vector

Figure 12:
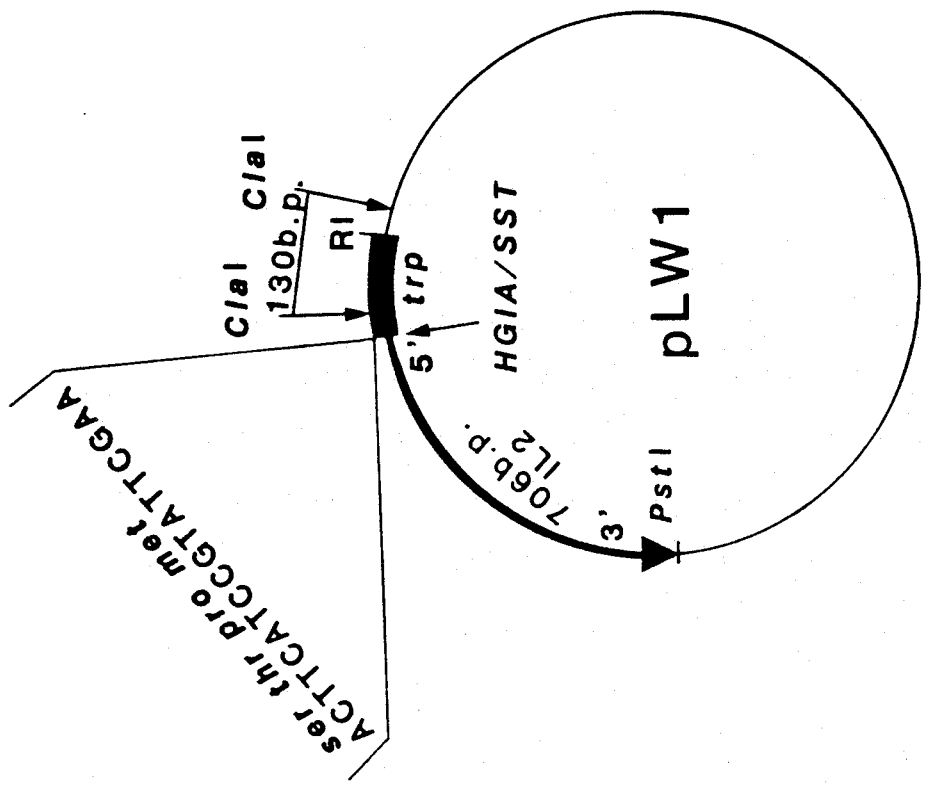
FIG. 12 is a diagram of the plasmid pLW1 which contains the human interleukin-2 (IL-2) gene under the control of the E. coli trp promoter
Figure 13:
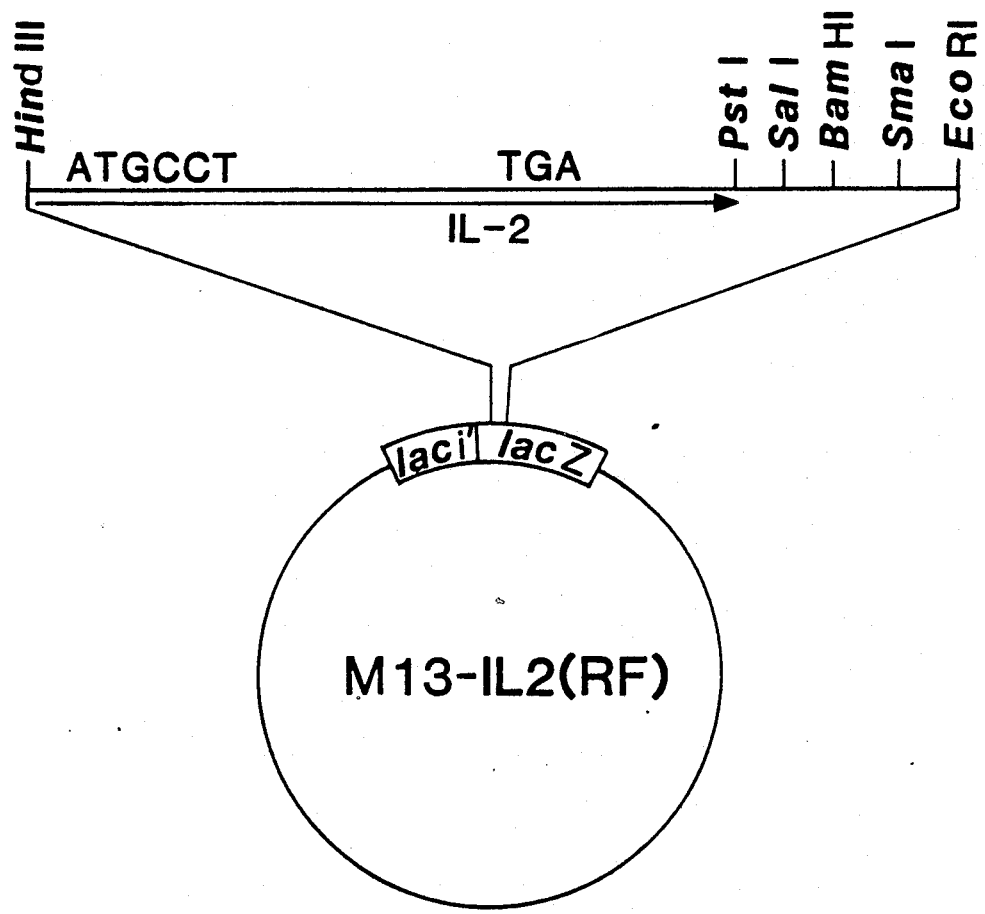
FIG. 13 is a restriction map of phage clone M13-IL2.

The IL-2 gene was cloned into M13mp9 as described in Example 1 using the plasmid pLW1 (FIG. 12) containing the IL-2 gene under the control of the *E. coli* trp promoter. A sample of pLW1 was deposited in the American Type Culture Collection, 12301 Parklawn Drive, Rockville, Md. 20852, U.S.A., on 4 Aug. 1983 and has been assigned ATCC number 39,405. The restriction map of one clone (designated M13-IL2) containing the IL-2 insert is shown in FIG. 13. Single-stranded phage DNA was prepared from clone M13-IL2 to serve as a template for oligonucleotide-directed mutagenesis.

EXAMPLE 15

Oligonucleotide-directed Mutagenesis

As indicated previously, IL-2 contains cysteine residues at amino acid positions 58, 105 and 125. Based on the nucleotide sequences of the portions of the IL-2 gene that contain the codons for these three cysteine residues three oligonucleotide primers were designed and synthesized for mutating the codons for these residues to codons for serine. These oligonucleotides have the following sequences.

CTTCTAGAGACTGCAGATGTTTC (DM27) to change cys 58,

CATCAGCATACTCAGACATGAATG (DM28) to change cys 105 and

GATGATGCTCTGAGAAAAGGTAATC (DM29) to change cys 125.

Forty picomoles of each oligonucleotide were kinased separately in the presence of 0.1 mM ATP, 50 mM Tris-HCl, pH 8.0, 10 mM MgCl$_2$, 5 mM DTT and 9 units of T$_4$ kinase in 50 μl at 37° C. for 1 hr. Each of the kinased primers (10 pmoles) was hybridized to 2.6 μg of ss M13-IL2 DNA in 15 μl of a mixture containing 100 mM NaCl, 20 mM Tris-HCl, pH 7.9, 20 mM MgCl$_2$ and 20 mM η-mercaptoethanol, by heating at 67° C. for 5 min and 42° C. for 25 min. The annealed mixtures were chilled on ice and then adjusted to a final colume of 25 μl of a reaction mixture containing 0.5 mM of each dNTP, 17 mM Tris-HCl, pH 7.9, 17 mM MgCl$_2$, 83 mM NaCl, 17 mM η-mercaptoethanol, 5 units of DNA polymerase I Klenow fragment, 0.5 mM ATP and 2 units of T$_4$ DNA ligase, incubated at 37° C. for 5 hr. The reactions were terminated by heating to 80° C. and the reaction mixtures used to transform competent JM103 cells, plated onto agar plates and incubated overnight to obtain phage plaques.

EXAMPLE 14

Screening and Identification of Mutagenized Phage Plaques

Plates containing mutagenized M13-IL2 plaques as well as 2 plates containing unmutagenized M13-IL2 phage plaques, were chilled to 4° C. and phage plaques from each plate were transferred onto two nitrocellulose filter circles by layering a dry filter on the agar plate for 5 min for the first filter and 15 min for the second filter. The filters were then placed on thick filter papers soaked in 0.2 N NaOH, 1.5 M NaCl and 0.2% Triton for 5 min, and neutralized by layering onto filter papers soaked with 0.5 M Tris-HCl, pH 7.5, and 1.5 M NaCl for another 5 min. The filters were washed in a similar fashion twice on filters soaked in 2×SSC, dried and then baked in a vacuum oven at 80° C. for 2 hr. The duplicate filters were pre-hybridized at 42° C. for 4 hr with 10 ml per filter of DNA hybridization buffer (5×SSC, pH 7.0, 4×Denhardts solution (polyvinylpyrolidine, ficoll and bovin serum albumin, 1× =0.02% of each), 0.1% SDS, 50 mM sodium phosphate buffer, pH 7.0 and 100 μg/ml of denatured salmon sperm DNA. $^{32}$P-labelled probes were prepared by kinasing the oligonucleotide primers with labelled ATP. The filters were hybridized to 0.1×10$^5$ cpm/ml of $^{32}$P-labelled primers in 5 ml per filter of DNA hybridization buffer at 42° C. for 8 hr. The filters were washed twice at 50° C. for 30 min each in washing buffers containing 0.1% SDS and 2×SSC, and twice at 50° C. for 30 min each with 0.1% SDS and 0.2×SSC. The filters were air dried and autoradiographed at −70° C. for 2–3 days.

Since the oligonucleotide primers DM28 and DM29 were designed to create a new DdeI restriction site in the mutagenized clones (FIG. 14), RF-DNA from a number of the clones which hybridized with each of these kinased primers were digested with the restriction enzyme DdeI. One of the mutagenized M13-IL2 placques which hybridized with the primer DM28 and has a new DdeI restriction site (M13-LW44) was picked and inoculated into a culture of JM103, ssDNA was prepared from the culture supernatant and dsRF-DNA was prepared from the cell pellet. Similarly, a plaque which hybridized with primer DM29 was picked (M13-LW46) and ssDNA and RF-DNA prepared from it. The oligonucleotide primer DM27 was designed to create a new PstI restriction site instead of a DdeI site. Therefore, the plaques that hybridized to this primer were screened for the presence of a new PstI site. One such phage plaque was identified (M13-LW42) and ssDNA and RF-DNA prepared from it. The DNA from all three of these clones were sequenced to confirm that the target TGT codons for cysteine had been converted to a TCT codon for serine.

EXAMPLE 17

Recloning of the Mutagenized IL-2 Gene for Expression in *E.coli*

Figure 14:
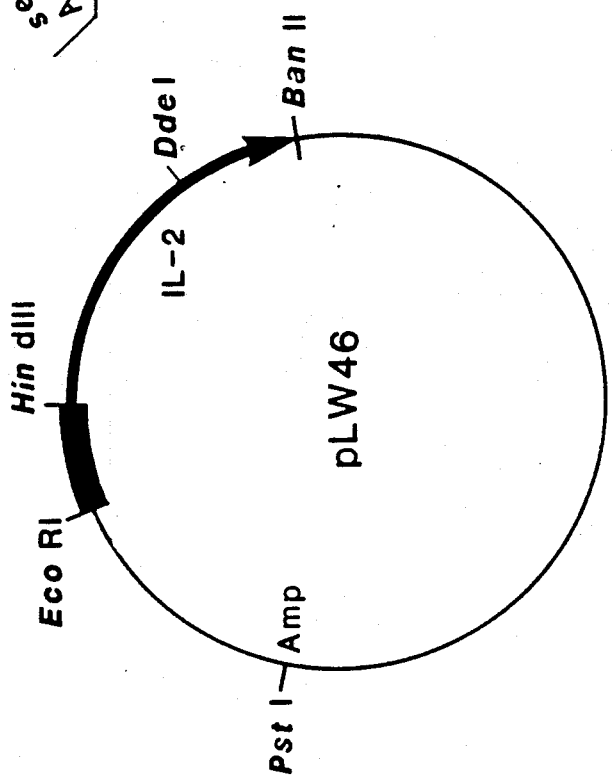
FIG. 14 is a restriction map of the plasmid pLW46.

RF-DNA from M13-LW42, M13-LW44 and M13-LW46 were each digested with restriction enzymes HindIII and BanII and the insert fragments purified from a 1% agarose gel. Similarly, the plasmid pTrp3 (FIG. 7) was digested with HindIII and BanII, the large plasmid fragment containing the trp promoter was purified on an agarose gel and then ligated with each of the insert fragments isolated from M13-LW42, M13-LW44 and M13-LW46. The ligated plasmids were transformed into competent *E. coli* K12 strain MM294. The plasmid DNAs from these transformants were analyzed by restriction enzyme mapping to confirm the presence of the plasmids pLW42, pLW44 and pLW46. FIG. 14 is a restriction map of pLW46. When each of these individual clones were grown in the absence of tryptophane to induce the trp promoter and cell free extracts analyzed on SDS-polyacrylamide gels, all three clones, pLW42, pLW44 and pLW46, were shown to synthesize a 14.5 kd protein similar to that found in the positive control, pLW21, which has been demonstrated to synthesize a 14.4 kd IL-2 protein. When these same extracts were subjected to assay for IL-2 activity on mouse HT-2 cells, only clones pLW21 (positive control) and pLW46 had significant amounts of IL-2 activity (Table II below), indicating that cys 58 and cys 105 are necessary for biological activity and changing them to serines (pLW42 and pLW44 respectively) resulted in the loss of biological activity. Cys 125 on the other hand must not be necessary for biological activity because changing it to ser 125 (pLW46) did not affect the biological activity.

TABLE II

| Clones | IL-2 Activity (μ/ml) |
|---|---|
| pIL2-7 (negative control) | 1 |
| pLW21 (positive control) | 113,000 |
| pLW42 | 660 |
| pLW44 | 1,990 |
| pLW46 | 123,000 |

FIG. 15a shows the nucleotide sequence of the coding strand of clone pLW46. As compared to the coding strand of the native human IL-2 gene clone pLW46 has a single base change of G→C at nucleotide 374. FIG. 15b shows the corresponding amino acid sequence of the IL-2 mutein encoded by pLW46. This mutein is designated IL-2$_{ser125}$ As compared to native IL-2 the mutein has a serine instead of a cysteine at position 125, has an initial N-terminal methionine (which is processed off), and lacks the initial N-terminal alanine of the native molecule.

A sample of *E. coli* K12 strain MM294 transformed with pLW46 was deposited in the American Type Culture Collection, 12301 Parklawn Drive, Rockville, Md. 20852, U.S.A. on 26 Sept. 1983 and has been assigned ATCC Number 39,452.

Examples 18 and 19 describe the preparation of an alternative and preferred vector for expressing IL-2$_{ser125}$.

EXAMPLE 18

Construction of Ala-IL-2 Expression Vector pLW32

Figure 16:
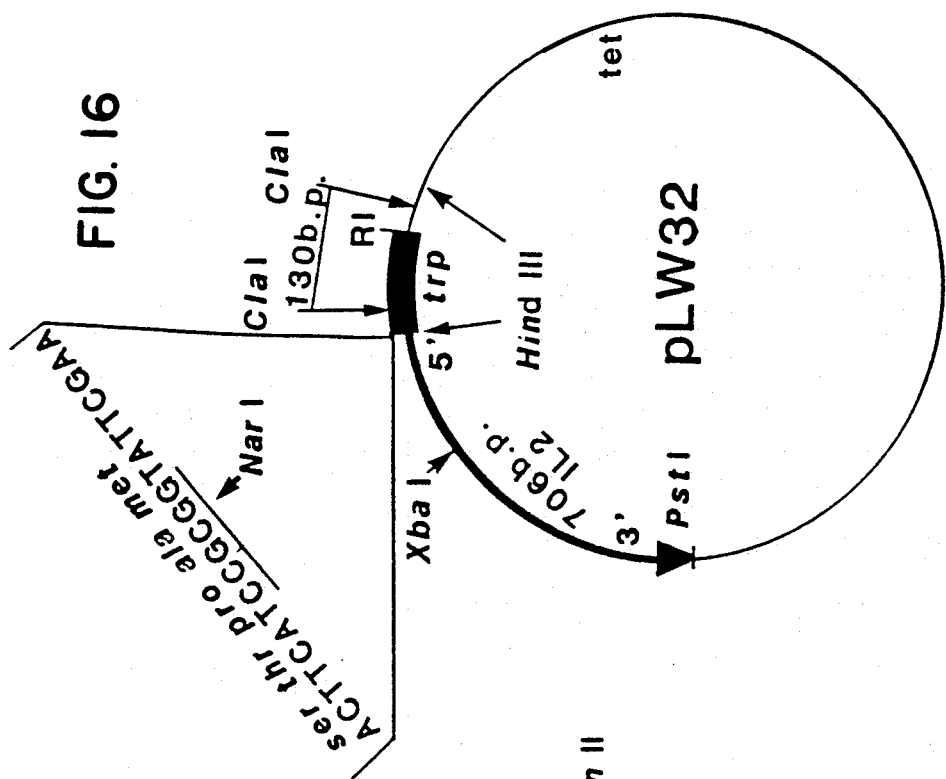
FIG. 16 is a diagram of the plasmid pLW32.

A codon (GCG) for alanine was inserted immediately after the initiation codon of the IL-2 gene of pLW1 by oligonucelotide-directed mutagenesis as follows. The oligonucleotide primer, 5'-GAAGTAGGCG-CCATAAG-3', was kinased, hybridized to ssM13-IL2 DNA, and extended using the general procedure of Example 15 to form a mutational heteroduplex. In addition to the insertion of the GCG codon, the mutagenesis generated a new NarI restriction site in the gene. The heteroduplex was converted to closed circular heteroduplex and the circular heteroduplexes were used to transform competent JM103 cells and plated onto agar plates and incubated as in Example 15. The plates were screened to identify mutagenized M13-IL2 by the procedure of Example 16. One mutagenized phage, identified as M13-LW32, was selected for use in additional cloning and RF-DNA was prepared from it. FIG. 16 is a diagram of plasmid pLW32.

EXAMPLE 19

Construction of Ala-IL-2$_{ser125}$ Expressing Clone pLW55

Figure 17:
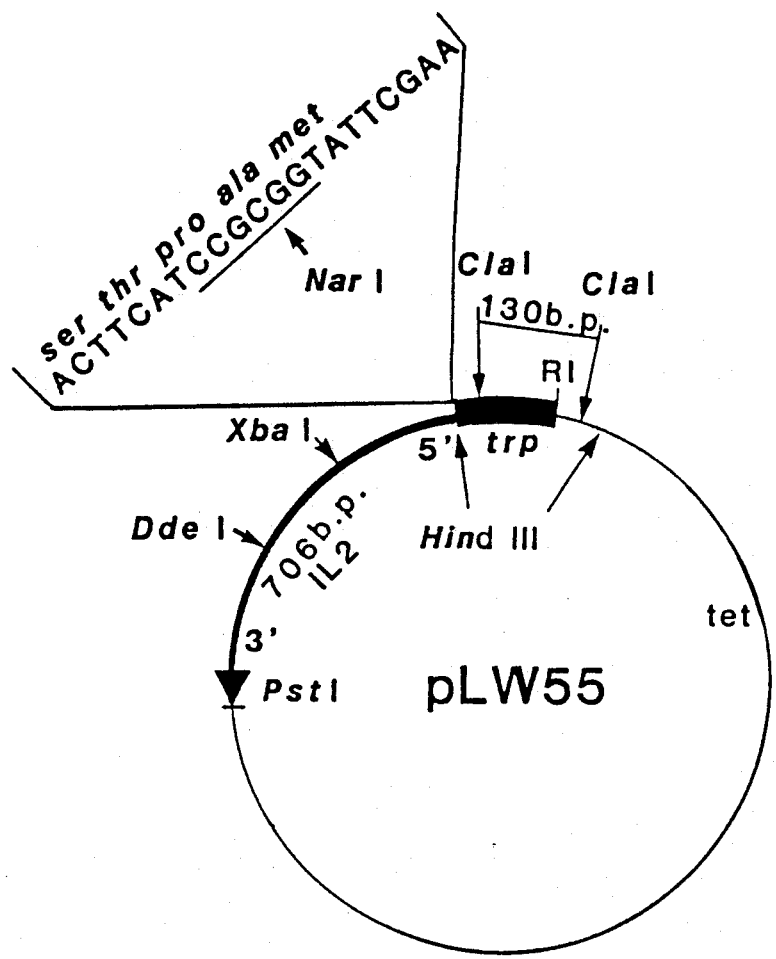
FIG. 17 is a diagram of the plasmid pLW55.

RF-DNA from M13-LW46 (Examples 16 and 17) was digested with XbaI and PstI and the 530 bp fragment containing the carboxy terminal coding region of the IL-2$_{ser125}$ gene was purified from an agarose gel. Similarly, pLW32 was digested with XbaI and PstI and the large fragment consisting of the plasmid vector and the ala-IL-2 N-terminal coding sequence was purified. The two purified DNA fragments were pooled and ligated using T$_4$ DNA ligase. The ligated DNA was transformed into competent *E. coli* K-12 strain MM294. Tetracycline resistant transformants were analyzed by restriction enzyme mapping for the presence of a plasmid containing an ala-IL-2$_{ser125}$ gene, identified as pLW55, which has a new DdeI site not found in pLW32. FIG. 17 is a diagram of pLW55. Cell free extracts of bacterial culture containing pLW55 were found to contain over 10$^5$ units of IL-2 activity per ml by the HT-2 cell assay, J. Watson, supra, and S. Gillis, supra. Ala-IL-2$_{ser125}$ protein is identical to the IL-2$_{ser125}$ molecule shown in FIG. 15(b) except that the former includes the initial N-terminal alanine of the native molecule.

A sample of *E. coli* K-12 strain MM294 transformed with pLW55 was deposited in the American Type Culture Collection on 18 Nov. 1983 and has been assigned ATCC number 39,516.

EXAMPLE 20

Ala-IL-2$_{ser125}$ Production and Purification

*E. coli* transformed with pLW55 were grown in a fermenter containing the following medium:

| | |
|---|---|
| (NH$_4$)$_2$SO$_4$ | 150 mM |
| KH$_2$PO$_4$ | 21.6 mM |
| Na$_3$ Citrate | 1.5 mM |
| ZnSO$_4$.7H$_2$O | 30 mM |
| MnSO$_4$.H$_2$O | 30 mM |
| CuSO$_4$.5H$_2$O | 1 mM | pH adjusted to 6.50 with 2.5 N NaOH autoclaved

| Sterile Additions (post autoclave) | |
|---|---|
| MgSO$_4$.7H$_2$O | 3 mM |
| FeSO$_4$ | 100 μM |
| L-tryptophan | 14 mg/l |
| Thiamine-HCl | 20 mg/l |
| Glucose | 5 g/l |
| Tetracycline | 5 mg/l |
| Ethanol | 2% |
| Casamino acids | 2% |

Dow Corning Antifoam polypropylene glycol, 20% solution, glucose, 50% solution, and KOH, 5N, were added on demand.

The pH of the fermenter was maintained at 6.8 with 5 N KOH. Residual glucose was maintained between 5–10 g/l, dissolved oxygen at 40%, and temperature at 37 ±1° C. The casamino acids (20% stock solution) to a concentration of 2% were added when the OD$_{680}$ was about 10. Harvest was made three hr after the OD reached about 20.

The harvested material was concentrated and homogenized as in Example 11. Following DTT-heat treatment, the material was centrifuged and the resulting paste was extracted with urea to a final concentration of 4M. The suspension was centrifuged and SDS was added to the solid phase to a concentration of 5%.

The solution was applied to a Sephacryl S-200 column and fractions containing IL-2 (by SDSPAE) were pooled. The pooled fractions were applied to a Whatman M-40 column packed with 18 micron Vydac C$_4$ 300 Å pore size bonded phase silica gel equilibrated in 0.1% TFA. The IL-2 mutein was eluted with a gradient of 40% to 60% 2-propanol, containing 0.1% TFA, in 160 min. Fractions containing highest IL-2 activities were pooled and found to have specific activities comparable to native IL-2.

Muteins of IL-2 in which the cysteine at position 125 has been deleted or replaced with another amino acid, such as the mutein IL-2$_{ser125}$ retain IL-2 activity. They may, therefore, be formulated and used in the same manner as native IL-2. Accordingly, such IL-2 muteins are useful for the diagnosis and treatment (local or systemic) of bacterial, viral, parasitic, protozoan and fungal infections; for augmenting cell-mediated cytotoxicity; for stimulating lymphokine activated killer cell activity; for mediating recovery of immune function of lymphocytes; for augmenting alloantigen responsiveness; for facilitating recovery of immune function in acquired immune deficient states; for reconstitution of normal immunofunction in aged humans and animals; in the development of diagnostic assays such as those employing enzyme amplification, radiolabelling, radioimaging, and other methods known in the art for monitoring IL-2 levels in the diseased state; for the promotion of T cell growth in vitro for therapeutic and diagnostic purposes for blocking receptor sites for lymphokines; and in various other therapeutic, diagnostic and research applications. The various therapeutic and diagnostic applications of human IL-2 have been investigated and reported in S. A. Rosenberg, E. A. Grimm, et al, A. Mazumder, et al, and E. A. Grimm and S. A. Rosenberg. IL-2 muteins may be used by themselves or in combination with other immunologically relevent B or T cells or other therapeutic agents. Examples of relevant cells are B or T cells, natural killer cells, and the like and exemplary therapeutic reagents which may be used in combination with the polypeptides of this invention are the various interferons, especially gamma interferon, B cell growth factor, IL-1 and the like. For therapeutic or diagnostic applications, they may be formulated in nontoxic, nonallergenic, physiologically compatible carrier media such as distilled water, Ringer's solution, Hank's solution, physiological saline and the like. Administrations of the IL-2 muteins to humans or animals may be oral or intraperitoneal or intramuscular or subcutaneous as deemed appropriate by the physician. The amount of IL-2 mutein administered will usually range between about $1 \times 10^4$ and $2 \times 10^8$ units.

EXAMPLE 21

Preparation and Purification of Human TNF

1. Induction of TNF

High density ($\geq 2 \times 10^6$ cells/ml) stationary HL-60 cells were centrifuged washed with RPMI 1640 medium in the absence of serum. and then resuspended at a density of $1 \times 10^7$ cells/ml. The cells were then treated with 100 ng/ml of a phorbol ester, 12-O-tradecanorylphorbol-13-acetate (TPA) for 30 min at 37° C. in a suspension culture with constant agitation. The cultures were centrifuged the supernatant was decanted the cells were resuspended at $1 \times 10^7$ cells/ml in RPMI. containing 10 μg/ml bacterial lipopolysaccharide (LPS) and 10 μM Ca ionophore (A23817) for 4 hr at 37° C. with constant agitation. The cells were spun down at 1200 rPm for 10 min. and the supernatants recentrifuged at 8000 rPm for 20 min. The resulting supernatant was used in the Purification scheme below to obtain native TNF.

2. Purification of TNF

About 4-8 liters of the supernatant prepared from induced HL-60 in the previous paragraph were concentrated via Amicon hollow fiber (1 square foot cartridge/10,000 MW cutoff) to approximately 300 ml. The concentrated culture fluid was centrifuged to remove cell debris, and supernatant adjusted with 30 mM ammonium bicarbonate buffer (pH 8.2) to a conductance of 6.2 mS. The solution was further concentrated by ultrafiltration using a PM10 (Amicon) membrane, and the concentrated fluid clarified by centrifugation ($20,000 \times g$ for 10 min).

The supernatant was then applied to a DEAE ion exchange column equilibrated in 30 mM ammonium bicarbonate/1 mM NaCl pH 8.2, and the column washed with the same buffer. Fractions were collected and Protein monitored at 280 nm. These unbound fractions were assayed using the L-929 cytotoxicity assay and those having TNF activity pooled and again concentrated by ultrafiltration.

The concentrate was applied to Sephadex G75 Superfine (Pharmacia) equilibrated in 30 mM ammonium bicarbonate buffer (PH 7.4). Unbound fractions obtained by washing With the same buffer were monitored at 280 nm and assayed for TNF. Fractions containing Peak TNF bioactivity Were lyophilized The lyophilized protein was resuspended in Laemmli SDS sample buffer and electrophoresed on SDS-Polyaorylamide gel. The gel was sliced into 2 mm sections, and the protein from each section was eluted by immersion in 1 ml of 30 mM ammonium bicarbonate buffer (PH 7.4) and overnight shaking at room temperature.

The sections containing the TNF bioactivity were applied onto a Vydac C-4 reverse phaqe HPLC column equilibrated in 0.1% trifluoroacetic acid (TFA). and the activity eluted using a linear gradient 0%-60% acetonitrile in 0.1% TFA. Protein was monitored at 280 nm and 214 nm. and the fractions bioassayed after lyophilization and suspended in 30 mM ammonium bicarbonate buffer PH 7.4. Fractions containing TNF activity were again lyophilized.

The resulting Protein was of sufficient Purity to be in sequence analysis. The sequence was determined using a gas Phase sequenator (Applied Biosystems Inc.). The sequence obtained from the first 22 amino acids is shown below.

| 1 | 2 | 3 | 4 | 5 | 6 | 7 | 8 | 9 |
|---|---|---|---|---|---|---|---|---|
| Val | Arg | Ser | Arg | Thr | Pro | Ser | Asp | Lys |

| 10 | 11 | 12 | 13 | 14 | 15 | 16 | 17 | 18 |
|---|---|---|---|---|---|---|---|---|
| Pro | Val | Ala | Val | Ser | Val | Ala | Asn | Pro |

| 19 | 20 | 21 | 22 |
|---|---|---|---|
| (Gln) | (Ala) | Glu | Gly |

In addition, the Purified Protein (from the G-75 gel) was tested with a modification of the L-929 cytotoxicity assay using alternate human tumor and normal cell lines as substrate. The G-75 fractions which were cytotoxic in this assay against L-929 cells were also cytotoxic against Hs939T (a melanoma line) BT-20 (breast carcinoma). A427 (lung carcinoma) HT-1OBO (colon carcinoma) and HT-29 (colon carcinoma). These fractions were not cytotoxic against Hs939sk (skin fibroblasts), HeLa cells (cervical carcinoma) Hs27F (foreskin fibroblasts) or COS7 (SV40-transformed monkey cells).

EXAMPLE 22

Preparation of the Coding Sequence

An intronless DNA sequence encoding human TNF was prepared by the procedure herein described. A human promyelocytic leukemia cell line which produces large amounts of TNF when induced, the HL-60 line, obtainable from ATCC. accession no. CCL 240, was used as the source of mRNA to obtain a cDNA library. Using oligomeric probes constructed on the basis of the protein sequence determined from TNF purified from these cells, this cDNA library was probed to retrieve the entire coding sequence for the protein.

1. Preparation of Enriched mRNA

Total messenger RNA was extracted and purified from HL-60 cells as follows: HL-60 cells were induced for TNF production as set forth in D.l.a. and the 4-hr cell suspension harvested by centrifugation. Total cytoplasmic ribonucleic acid (RNA) was isolated as follows; all steps are at 4° C. Cells are washed twice in pBS (phosphate buffered saline) and resuspended in IHB (140 mM NaCl, 10 mM Tris, 1.5 mM MgCl$_2$, pH 8) containing 10 mM vanadyl adenosine complex (Berger, S. L., et al, *Biochem* (1979) 18:5143).

A non-ionic detergent of the ethylene oxide polymer type (NP-40) was added to 0.3% to lyse the cellular but not nuclear membranes. Nuclei were removed by centrifugation at 1,000×g for 10 min. The post-nuclear supernatant was added to an equal volume of TE (10 mM Tris, 1 mM ethylenediaminetetraacetic acid (EDTA), pH 7.5) saturated phenol/chloroform (1:1) containing 0.5% sodium dodecyl sulfate (SDS) and 10 mM EDTA. The supernatant was re-extracted 4 times and phase separated by centrifugation at 2.000×g for 10 min. The RNA was precipitated by adjusting the sample to 0.25 M NaCl, adding 2 volumes of 100% ethanol and storing at −20° C. The RNA was pelleted at 5.000×g for 30 min. washed with 70% and 100% ethanol and dried. Polyadenylated (Poly A+) messenger RNA (mRNA) was obtained from the total cytoplasmic RNA by chromatography on oligo dT cellulose (Aviv, J., et al, *Proc Natl Acad Sci* (1972) 69:1408-1412): The RNA was dissolved in ETS (10 mM Tris, 1 mM EDTA, 0.5% SDS, pH 7.5) at a concentration of 2 mg/ml. This solution was heated to 65° C. for 5 min. then quickly chilled to 4° C. After bringing the RNA solution to room temperature. it was adjusted to 0.4M NaCl and slowly passed through an oligo dT cellulose column previously equilibrated with binding buffer (500 mM NaCl, 10 mM Tris, 1 mM EDTA, pH 7.5). The flow-through was passed over the column twice more, and the column washed with 10 volumes of binding buffer. Poly A+ mRNA was eluted with aliquots of ETS, extracted once with TE-saturated phenol chloroform and precipitated by the addition of NaCl to 0.2M and 2 volumes of 100% ethanol. The RNA was reprecipitated twice, washed once in 70% and then in 100% ethanol prior to drying.

The poly A+ mRNA was fractionated on a sucrose gradient in 10 mM Tris-HCl pH 7.4, 1 mM EDTA. 10 mM NaCl and 0.1% SDS. After centrifugation in a Beckman SW40 rotor at 38,000 rpm for 17 hr, mRNA fractions were recovered from the gradient by ethanol precipitation. The fractions containing TNF mRNA were identified by injecting the mRNA into oocytes and assaying the oocyte extracts for cytotoxic activity. Fractions containing peak activity were pooled for use in cDNA library construction.

2. Construction of a cDNA Library cDNA was made from the enriched 16S mRNA fraction using oligo dT priming of the poly A tails and AMV reverse transcriptase employing the method of Okayama, H., et al, *Mol Cell Biol* (1983) 3:280, incorporated herein by reference. This method results in a higher proportion of full length clones and effectively uses as host vector portions of two vectors therein described, and readily obtainable from the authors, pcDV1 and pL1. The resulting vectors contain the insert between vector fragments containing proximal BamHI and XhoI restriction sites; the vector contains the pBR322 origin of replication, and Amp resistance gene.

Other methods of preparing cDNA libraries are of course, well known in the art. One, now classical method uses oligo dT primer, reverse transcriptase, tailing of the double stranded cDNA with poly dG. and annealing into a suitable vector, such as pBR322 or a derivative thereof, which has been cleaved at the desired restriction site and tailed with poly dC. A detailed description of this alternate method is found, for example, in U.S. Ser. No. 564,224, filed Dec. 20, 1983 and assigned to the same assignee incorporated herein by reference.

In the method used here, the enriched mRNA (5 μg) was denatured by treatment with 10 mM methyl mercury at 22° C. for 5 min and detoxified by the addition of 100 mM 2-mercaptoethanol (payvar. F., et al, *J Biol Chem* (1979) 254:7636-7642). Plasmid pcDVI was cleaved with KpnI, tailed with dTTP, and annealed to the denatured mRNA. This oligo dT primed mRNA was treated with reverse transcriptase and the newly synthesized DNA strand tailed with dCTP, Finally, the unwanted portion of the pcDV1 vector was removed by cleavage with HindIII. Separately, pL1 was cleaved with PstI. tailed with dGTP cleaved with HindIII, and then mixed with the poly T tailed mRNA/cDNA complex extended by the pcDV1 vector fragment ligated with *E. coli* ligase and the mixture treated with DNA polymerase I (Klenow) *E. coli* ligase and RNase H. The resulting vectors are transformed into *E. coli* K12 MM294 to Amp ®.

3. Selection of probe

Oligomers complementary to the coding sequence for amino acids 8–12 of the purified TNF sequence were prepared. Because of codon redundancy, a total of sixty-four 14-mers are candidates for complementation to the messenger encoding this portion. All sixty-four 14-mers were prepared, and divided into four pools of sixteen. Each pool was mixed with the sucrose gradient size-fractionated enriched mRNA preparation prepared as above, and the mixture injected into the oocyte translation system. Controls were run using untreated messenger RNA. The proteins produced in the oocyte systems were subjected to L-929 cytotoxicity assay ($^{35}$S release) and the proteins derived from oocytes injected with control and with a mixture of mRNA with three of the oligomer pools showed activity. In this "hybrid arrest" assay, only the oocyte injected with messenger which had been treated with the pool having the sequence $$GC(_T^G)AC(_A^C)GGCTTGTC$$
$$\phantom{GC(}C\phantom{)AC(}G$$

was inactive. The specificity of this oligomer pool was further determined using "dot blot" hybridization with enriched mRNA prepared as above from both induced and uninduced HL-60 cells, as well as the corresponding mRNA fraction obtained from cells known to be producers of lymphotoxin. This pool hybridized well to the induced mRNA, but failed to hybridize with the corresponding fractions from the uninduced or lymphotoxin producing cells. However Northern blots using the kinased pool as probe demonstrated that it contained sequences which cross hybridize with the 18S (ribosomal) RNA fraction and to pBR322 DNA.

The successful pool was therefore further fractionated by synthesizing its members as eight pairs of 14-mers, each of which was used in the "hybrid arrest" assay performed as set forth above. Only the pair with the sequence $$GC(_T^C)ACAGGCTTGTC$$

was successful in inhibiting the synthesis of TNF in the oocytes. Dot blot experiments using the fractionated induced HL-60 mRNA fraction, induced total HL-60 poly A+ RNA, uninduced HL-60 poly A+ RNA, and pBR322 DNA confirmed the specificity of the foregoing 14-mer pair and the inability of the remaining pairs to hybridize to the desired messenger.

4. Recovery of the Coding Sequence

The cDNA library was probed with the 14-mer pair identified above. Twenty-eight colonies which hybridized with probe were picked cultured, and the plasmid DNA isolated. Plasmids containing inserts of sufficient length to encode the entire sequence were selected and several were assayed for the correct sequence using hybrid translation in combination with the $^{35}$S release version of the cytotoxic assay, as described below. Hybrid translation assays use the test sequence to retrieve the correct mRNA from unfractionated preparations as verified by assaying the protein produced by the oocyte translation system injected with the retrieved messenger.

The plasmid cDNA to be tested is bound to filters, and the filters treated with poly A+ RNA isolated from induced HL-60 cells. The filters are then eluted and the eluates injected into the oocyte translation system. The oocytes are extracted for protein, which is then tested in the $^{35}$S version of the L-929 cytotoxic assay. The results for several hybridizing clones, designated E2-E4 E6 and E8 are shown below:

| Sample | % Release of $^{35}$S |
|---|---|
| E1 | 7 |
| E2 | 23 |
| E3 | 32 |
| E4 | 33 |
| E6 | 26 |
| E8 | 11 |
| pBR322 | 9 |
| A+ | 34 |
| B+ | 24 |

(A+ and B+ are controls using enriched mRNA as obtained by sucrose gradient; E1 and pBR322 are negative controls.)

Figure 19:
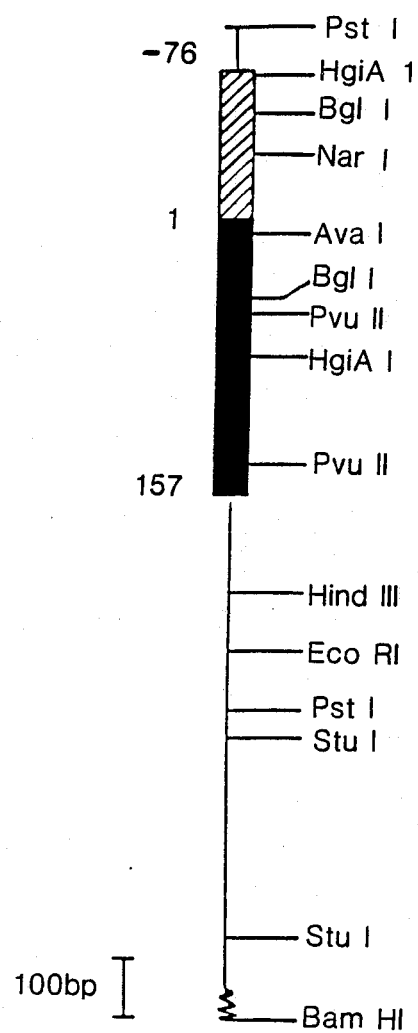
FIG. 19 shows a restriction map of the PE4 insert.
Figure 21:
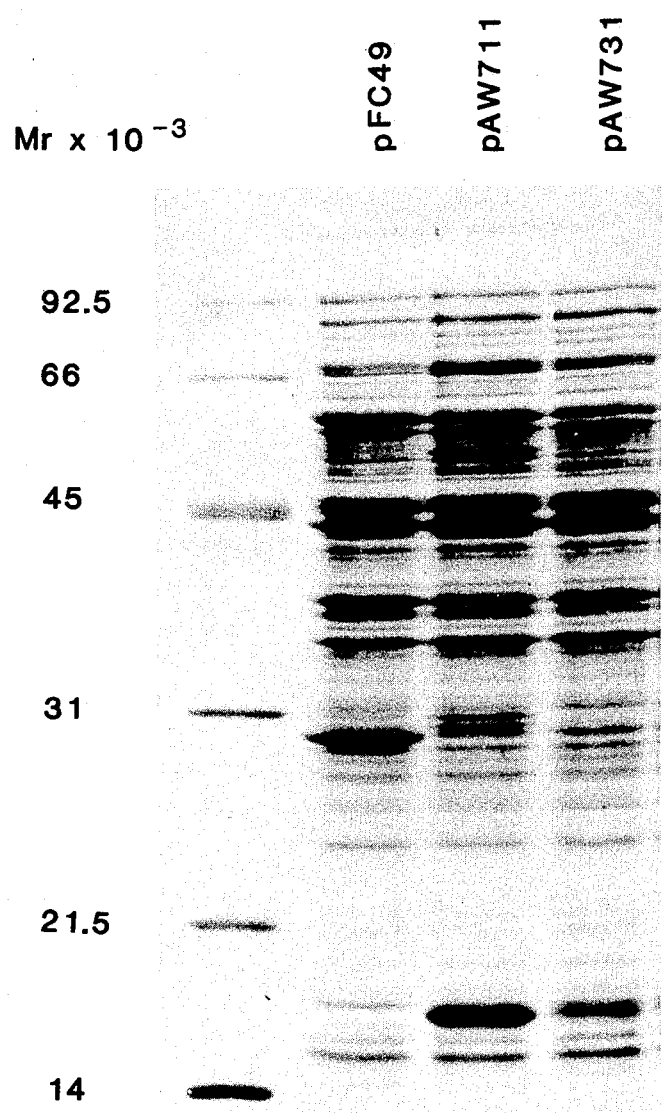
FIG. 21 shows the single 17,000 dalton protein band corresponding to ser 69 TNF in the extracts of clone pAW711 and pAW 731.

Restriction analysis and partial sequencing of the inserts indicated that two candidate plasmids, pE4 and pB11 were likely to have the complete TNF encoding sequence. The results of this analysis for pE4 are shown in FIG. 19. PE4 was deposited at ATCC on Oct. 15, 1984 and has accession no. 39,894.

pE4 was sequenced and the correct reading frame for TNF identified by matching the amino acid sequence deduced from translation of all three possible reading frames with the known N-terminal sequence of the native mature TNF as determined by N-terminal sequencing of the purified protein (see FIG. 18). The amino acids in the mature protein are numbered starting with the valine at position 1. As noted above, homology was not complete. However, the high degree of homology indicated that the correct cDNA had been chosen. Verification of the experimentally determined restriction cleavage sites shown in FIG. 19 is also provided. The HindIII site upstream of the 3' PstI site in the 1.1 kb PstI fragment is downstream of the stop codon, thus permitting excision of the coding sequence as a HindIII cassette, after modification of the upstream region as described below.

5. Characteristics of Human TNF as Determined from the DNA Sequence

As deduced from the cDNA sequence set forth in FIG. 18, the mature TNF protein contains 1-57 amino acid residues and has a molecular weight, without glycosylation, of approximately 17,354. The leader sequence apparently contains roughly 76 amino acids, beginning with the first available Met start codon. There are 2 cysteine residues, at positions 69 and 101.

EXAMPLE 23

Modification of the N-terminal Codons in pE4

It was convenient, in effecting the expression of the mature protein, to introduce an ATG start codon immediately preceding the GTC sequence encoding N-terminal valine of the mature protein (designated 1 in FIG. 18). as well as to provide a HindIII site immediately upstream of the ATG for ligation into suitable host expression vectors. This was accomplished by site-directed mutagenesis in a manner analogous to that described in Examples 1, 2 and 5.

The DNA fragment containing the upstream portion of the coding sequence was excised from pE4 by digestion with PstI. isolated by agarose gel electrophoresis, recovered by electroelution, and ligated into the PstI site of bacteriophage M13mp18.

The ligated phage were transduced into frozen competent E.coli K12 strain DG98 (ATCC #39768) and cultured by plating on media containing $5 \times 10^{-4}$ M isopropyl thiogalactoside (IPTG) obtained from Sigma Chem. (St Louis, Mo.) and 40 μg/ml X-gal. Non α-complementing white plaques were picked onto fresh media. Mini-cultures were screened for recombinant single strand phage DNA containing inserts of the expected (1.1 kb) size. The structure of the desired recombinant phage, designated clone 4.1, was confirmed using restriction analysis.

A chemically synthesized. Purified. 33-mer oligodeoxyribonucleotide having the sequence:

5'-GAAGATGATCTGAC-
CATAAGCTTTGCCTGGGCC-3' was used to introduce a HindIII restriction enzyme site and an ATG-initiation codon before the GTC codon coding for the first amino acid (valine) of the mature TNF protein.

Ten picomoles of the oligonucleotide were hybridized to 2.6 μg of ss clone 4.1 DNA in 15 μl of a mixture containing 100 mM NaCl, 20 mM Tris-HCl, pH 7.9, 20 mM MgCl$_2$ and 20 mM β-mercaptoethanol, by heating at 67° C. for 5 min and 42° C. for 25 min. The annealed mixtures were chilled on ice and then adjusted to a final volume of 25 μl of a reaction mixture containing 0.5 mM of each dNTP, 17 mM Tris-HCl, pH 7.9, 17 mM MgCl$_2$, 83 mM NaCl, 17 mM β-mercaptoethanol, 5 units of DNA polymerase I Klenow fragment, incubated at 37° C. for 1 hr. The reactions were terminated by heating to 80° C. and the reaction mixtures used to transform competent DG98 cells. Plated onto agar plates and incubated overnight to obtain phage plaques.

Plates containing mutagenized clone 4.1 plaques as well as 2 plates containing unmutagenized clone 4.1 phaqe plaques. Were chilled to 4° C. and phage plaques from each plate were transferred onto 2 nitrocellulose filter circles by layering a dry filter on the agar plate for 5 min for the first filter and 15 min for the second filter. The filters were then placed on thick filter papers soaked in 0.2N NaOH, 1.5M NaCl and 0.2% Triton X-100 for 5 min, and neutralized by layering onto filter papers soaked with 0.5M Tris-HCl, pH 7.5, and 1.5M NaCl for another 5 min. The filters were washed in a similar fashion twice on filters soaked in 2×SSC, dried and then baked in a vacuum oven at 80° C. for 2 hr. The duplicate filters were pre-hybridized at 42° C. for 4 hr with 10 ml per filter of DNA hybridization buffer (5×SSC, pH 7.0, 4×Denhardts solution (polyvinylpyrrolidine, ficoll and bovin serum albumin, 1x=0.02% of each), 0.1% SDS 50 mM sodium phosphate buffer. pH 7.0 and 100 μg/ml of denatured salmon sperm DNA. $^{32}$-labeled probes were prepared by kinasing the primer with labeled ATP. The filters were hybridized to 5×10$^6$ cpm/ml of $^{32}$P-labeled primer in 1-5 ml per filter of DNA hybridization buffer at 64° C. for 8 hr.

The filters were washed once at room temperature for 10 min in 0.1% SDS. 20 mM sodium phosphate (buffer) and 6×SSC; once at 37° C. for 20 min in buffer and 2×SSC; once at 50° C. for 20 min in buffer and 2×SSC; and finally at 60° C. for 20 min in buffer and 1×SSC. The filters were air dried and autoradiographed at −70° C. for 4 hr.

Since the oligonucleotide primer was designed to create a new HindIII restriction site in the mutagenized clones, RF-DNA from a number of the clones which hybridized with the primer were digested with this restriction enzyme. One of the mutagenized clone 4.1 plaques which has a new HindIII restriction site (M13-AW701) was picked and inoculated into a culture of DG98, ssDNA was prepared from the culture supernatant and dsRF-DNA was prepared from the cell pellet. The correct sequence is confirmed by dideoxy sequencing.

The correctly synthesized strands were isolated and cleaved with PstI and HindIII (partial) or with HindIII alone for ligation into expression vectors.

EXAMPLE 24

Expression of TNF

For procaryotic expression the coding sequence (along with some 3' untranslated nucleotides) was excised from dsM13-AW701 in two ways:

In the first method, the dsM13-AW701 was digested with PstI and then digested partially with HindIII to obtain the HindIII-PstI TNF coding sequence. (partial HindIII digestion is required because there are several HindIII sites in M13-AW701.) The partial digestion of the DNA fragment can be accomplished by using one-tenth the amount of restriction enzyme required for complete digestion of the DNA. The mixture was incubated at the appropriate temperature for the enzyme and aliquots of the digestion mixture were removed at 10 min intervals for up to 1 hr. The aliquots were then loaded onto a gel and the DNA fragments analyzed. The time point that provided the highest yield of the DNA fragment needed was chosen for a preparative digestion with the restriction enzyme and the appropriate fragment purified from the gel by electroelution.

The PstI/BamHI fragment containing the 3'-noncoding sequence of the TNF gene (see FIG. 2) was purified from pE4 following digestion of the DNA with the enzymes PstI and BamHI.

Together, the HindIII/PstI and PstI/BamHI fragments comprise the coding sequence plus a 600 bp 3' untranslated portion of DNA. The two fragments were ligated into HindIII/BamHI digested host vector pTRP3 as follows:

pTRP3 (ATCC 39946), contains the E.coli trp promoter and ribosome binding site. pTRP3 was digested with HindIII and BamHI, and the vector fragment purified on agarose gel. The isolated fragment was then ligated with the above HindIII/PstI and PstI/BamHI segments in a 3-way ligation, and the mixture used to transform E. coli MM294 to Amp®, giving pAW701.

In a second method. dsM13-AW701 was digested with HindIII and the fragment containing the gene isolated on agarose gel. The isolated fragment was ligated with HindIII cleaved, BApped pTRP3, and transformed into E.coli MM294 to obtain pAW702.

pFC54.t (ATCC 397B9) or pPLOP (ATCC 39947). containing the P$_L$ promoter and bacillus positive retroregulatory sequence can also be used as host vectors. These vectors are digested with HindIII and BamHI and the large plasmid fragments containing the control sequences purified on agarose gel. The HindIII/PstI and PstI/BamHI portions of the TNF gene, prepared as set forth above, are ligated, in a three way ligation, into the HindIII and BamHI sites of these vectors resulting in plasmids pAW711 and pAW712 respectively. Alternatively, the purified HindII fragment from mutagenized pE4 is ligated into HindIII cleaved. BApped pFC54.t or pPLOP to give pAW713 and pAW714, respectively. Plasmid pAW711 was deposited with ATCC on Nov. 8, 1984 and has accession no. 39,918.

pAW701 and pAW702 were transferred into E.coli MM294 and the cultures grown under conditions which suppress the trp promoter. Upon induction by tryptophan depletion, production of TNF was initiated. In an analogous fashion, pAW711 was constructed and transferred into E.coli MC1000-39531, and the cells were induced by high temperature. After several hours of culturing under induction conditions, the cells were sonicated and the sonicates verified to contain TNF by the L-929 cytotoxicity assay. The results are:

| Plasmid | U/ml |
| --- | --- |
| 701 | $1.3 \times 10^4$ |
| 702 | $1.3 \times 10^4$ |
| 711 | $2 \times 10^5$ |

Units of TNF activity are as defined below in Example 29.

The vector pB11 isolated from the cDNA library above, contains the SV40 promoter in operable linkage to the TNF coding sequence. All of the 28 positively hybridizing colonies would be expected to contain this linkage, including, specifically pE4 and pB11, and are thus capable of expression in suitable mammalian hosts. Accordingly, pB11 was used to transform COS-7 monkey kidney cells, and the cells cultured under conditions which effect the induction of the SV40 promoter. As the signal sequence is still present in pB11, and functions in mammalian cell systems, the TNF was secreted into the medium. TNF was assayed in the supernatant above the monolayered COS-7 cells by $^{35}$S release from L-929 cells, with results as follows:

| Plasmid | $^{35}$S Release (cpm) |
| --- | --- |
| B11 | 22,763 |
| E9 (neg control) | 2,739 |
| -DNA | 2,565 |

EXAMPLE 25

Preparation of Coding Sequence and Expression Vectors for TNF Muteins

Clone 4.1 prepared by PstI treatment of pE4 as described in Example 23 was subjected to site-specific mutagenesis substantially as described in Example 23, but using as primer 5'-CATGGGTGCTCGGGCTGCCTT-3', which is complementary to the sequence adjacent to the cysteine at position 69, but contains nucleotides complementary to that codon so as to effect a change from TGC to AGC. Mutagenized plaques were identified and confirmed by sequencing as described above. One plaque containing the desired mutation, MB-AW731 was digested with AvaI and PstI, and the fragment ligated into PstI/AvaI digested pAW711. The ligation mixture was transferred into E.coli MC1000-39531 to Amp ® and the transformants screened with the primer probe for the correct sequence. One colony, designated pAW731, was used for expression of the modified sequence. pAW731 was deposited with ATCC Jan. 25, 1985 and has accession no. 53007.

In an analogous manner, pAW741, an expression vector for ser101 TNF was prepared using the primer CAAGAGCCCCTCTCAGAGGGAG.

EXAMPLE 26

Expression of the Coding Sequence for and Activity of TNF Muteins

E.coli MC1000-39531 harboring pAW731 was grown and induced at high temperature in the manner set forth in Example 24. The sonicates from the induced cells were assayed and found to have approximately the same TNF activity per ml as the pAW711 transformants. However, SDS analysis showed that the amount of 17 kD TNF protein in these extracts is about 5x less, showing that the specific activity of $Ser_{69}$ TNF is higher than that of the natural or wild-type recombinant TNF protein.

EXAMPLE 27

Expression of the Coding Sequence for Recombinant $Ser_{69}$ $Ser_{101}$ Human TNF Mutein Plasmid pAW731 (ser69) is digested with HindIII and HincII, and the small HindIII-HincII fragment containing the ser69 mutation is purified on agarose gel. Similarly, plasmid pAW732 (ser101) is digested with the enzymes HincII and BamHI, and the HincII-BamHI fragment containing the ser101 mutation is purified. The previously purified HindIII-BamHI vector fragment from pFC54.t is then ligated with the HindIII-HincII (ser69) fragment and the HincII-BamHI (ser101) fragment to generate the ser69ser101 TNF clone, pAW735. This dimutein, ser69ser101 TNF, is less likely to dimerize on purification due to the absence of any free cysteines.

EXAMPLE 28

Cysteine Residues in Native or Wild-Type Human TNF are not Needed for Biological Activity Purified (95%) unaltered protein was reduced and alkylated by treating with DTT and iodoacetate according the protocol set forth below. While the untreated protein had an activity in U/ml of $2.6 \times 10^4$, reduced or reduced alkylated protein had activities of $4.4$–$4.8 \times 10^4$ U/ml:

| Treatment | Activity |
| --- | --- |
| No DTT | $2.6 \times 10^4$ |
| 0.1 mM DTT | $3.3 \times 10^4$ |
| 1 mM DTT | $4.8 \times 10^4$ |
| 2 mM DTT | $3.9 \times 10^4$ |
| 10 mM DTT | $1.2 \times 10^4$ |
| 20 mM DTT | $1.7 \times 10^4$ |
| buffer + 2.4 mM IAA | $1.5 \times 10^4$ |
| 1 mM DTT + 2.4 mM IAA | $4.4 \times 10^4$ |

The above data demonstrates that the cysteines in the wild-type recombinant human TNF are not required for biological activity, thus, one or both of the cysteines may be deleted or substituted with another amino acid as provided within the scope of the invention.

EXAMPLE 29

Cytotoxic Assay procedure for TNF

The L-929 assay system is an improved convenient in vitro assay which permits rapid measurement of TNF activity. Its degree of correlation with the in vivo tumor necrosis assay of Carswell (supra) is, at present, unknown; however, as it utilizes murine tumor cells specifically, the correlation is expected to be high. The protein designated lymphotoxin in EPO publication no. 0100641 also gives activity in this assay. The assay is similar in concept to that disclosed in U.S. Pat. No. 4,457,916 which used murine L-M cells and methylene blue staining. However, the L-929 assay has been shown herein to correlate (for HL-60-derived TNF) with human tumor cell line cytotoxicity.

In the L-929 assay system. L-929 cells are prepared overnight as monolayers in microtiter plates. The test samples are diluted 2-fold across the plate UV irradiated, and then added onto the prepared cell monolayers. The culture media in the wells are then brought to 1 μg/ml actinomycin D. The plates are allowed to incubate 18 hr at 37° C. and the plates are scored visually under the microscope. Each well is given a 25, 50, 75 or 100% mark signifying the extent of cell death in the well. One unit of TNF activity is defined as the reciprocal of the dilution at which 50% killing occurs.

In addition a more sensitive version of this assay was developed that monitors the release of $^{35}S$ labeled peptides from prelabeled cells, when treated with the test sample and actinomycin D. This version of the assay can be used to quantitate potency, e.g. to evaluate the relative potency of oocyte translated material. Briefly, actively growing L-929 cultures are labeled with $^{35}S$ methionine (200 μCi/ml) for 3 hr in methionine-free media supplemented with 2% dialyzed fetal calf serum. The cells are then washed and plated into 96 well plates incubated overnight, and treated the next day with 2-fold dilutions of test samples and 1 μg/ml actinomycin D. The cultures were then incubated at 37° C. for 18 hr. 100 μl supernatant aliquots from each well were then transferred onto another 96 well plate, acid (TCA) precipitated, and harvested onto glass fiber filters. The filters were washed with 95% ethanol, dried and counted. An $NP_{40}$ detergent control is included in every assay to measure maximum release of radioactivity from the cells. The percent $^{35}S$ release is then calculated by the ratio of the difference in count between the treated cells and untreated controls divided by the difference between $NP_{40}$ treated cells and untreated controls, i.e., by the ratio:

$$\% \text{ release} = \frac{\text{sample} - \text{cell control}}{NP_{40} - \text{cell control}} \times 100.$$

Higher TNF potency results in higher values of this ratio.

The TNF muteins of the invention are conveniently formulated into suitable therapeutic formulations which will typically includes a therapeutic effective amount of the mutein and a suitable physiologically acceptable carrier as described above with respect to the IL-2 muteins. Alternatively, other cytotoxic, antiviral or anti-cancer agents may be used in combination with the TNF muteins of the invention such as gamma interferon.

On Oct. 15, 1984, Applicants have deposited with the American Type Culture Collection, Rockville, Md., USA (ATCC) the plasmid pE4. described hererin ATCC accession no. 39,894. On Nov. 8, 1984, pAW711 was deposited and given ATCC accession no. 39,918. On Jan. 25, 1985, pAW731 was deposited and given ATCC accession no. 53,007. These deposits were made under the provisions of the Budapest Treaty on the International Recognition of the Deposit of Microorganisms for the purposes of patent procedure and the Regulations thereunder (Budapest Treaty). This assures maintenance of a viable culture for 30 years from date of deposit. The organisms will be made available by ATCC under the terms of the Budapest Treaty, and subject to an agreement between Applicants and ATCC which assures unrestricted availability upon issuance of the pertinent US patent. Availability of the deposited strains is not to be construed as a license to practice the invention in contravention of the rights granted under the authority of any government in accordance with its patent laws.

Modifications of the above described modes for carrying out the invention that are obvious to those of skill in the fields of genetic engineering, protein chemistry, medicine, and related fields are intended to be within the scope of the following claims.

We claim:

1. A synthetic mutein of a biologically active native protein which native protein has at least one cysteine residue that is free to form a disulfide link and is nonessential to said biological activity, said mutein having at least one of said cysteine residues substituted by another amino acid and said mutein exhibiting the biological activity of said native protein.

2. The synthetic mutein of claim 1 wherein there is only one of said cysteine residues comprised in the biologically active native proteins.

3. The synthetic mutein of claim 1 wherein said cysteine residues are replaced by serine, threonine, glycine, alanine, valine, leucine, isoleucine, tyrosine, phenylalanine, tryptophan, or methionine.

4. The synthetic mutein of claim 1 wherein said cysteine residues are replaced by serine or threonine.

5. The synthetic mutein of claim 1 wherein the mutein is unglycosylated.

6. A therapeutic formulation comprising an effective amount of the mutein of claims 1, 2, 3, 4 or 5, and at least one other anti-cancer or anti-viral compound.

7. The formulation of claim 6 wherein the anti-cancer or anti-viral compound is gamma interferon.

8. A structural gene having a DNA sequence that encodes a synthetic mutein of a biologically active native protein which native protein has at least one cysteine residue that is free to form a disulfide link and is nonessential to said biologically activity, said native mutein having at least one of said cysteine residues substituted by another amino acid and said mutein exhibiting the biological activity of said native protein.

9. A structural gene having a DNA sequence that encodes the synthetic mutein of claim 8 wherein there is only one of said cysteine residues comprised in the biologically active native protein.

10. A structural gene having a DNA sequence that encodes the synthetic mutein of claim 8 wherein said cysteine residues are substituted by serine, threonine, glycine, alanine, valine, leucine, isoleucine, histidine, tyrosine, phenylalanine, tryptophan or methionine.

11. A structural gene having a DNA sequence that encodes the synthetic mutein of claim 8 wherein said cysteine residues are substituted by serine or threonine.

12. A structural gene having a DNA sequence that encodes the synthetic mutein of claim 8 wherein the mutein is unglycosylated.

13. An expression vector that includes the structural gene of claim 1, 9, 10, 11 or 12 in a position that permits expression thereof.

14. A host cell or organism transformed with the expression vector of claim 13 and progeny thereof.

15. *E.coli* transformed with the expression vector of claim 13 and progeny thereof.

16. A process for making a synthetic mutein comprising culturing the host or progeny of claim 14 and harvesting the synthetic mutein from the culture.

17. A method for making a gene having a DNA sequence that encodes a synthetic mutein of a biologically active native protein which native protein has at least one cysteine residue that is free to form a disulfide link and is non-essential to said biological activity, said mutein having at least one of said cysteine residues substituted by another amino acid and said mutein exhibiting the biological activity of said native protein comprising:
- (a) hybridizing single-stranded DNA comprising a strand of a structural gene that encodes said protein with a mutant oligonucleotide primer that is complementary to a region of said strand that includes the codon for said cysteine residue or the anti-sense triplet paired with said codon, as the case may be, except for a mismatch with said codon or said antisense triplet which mismatch defines a triplet that codes for said other amino acid;
- (b) extending the primer with DNA polymerizes to form a mutational heteroduplex; and
- (c) replicating said mutational heteroduplex 18. The method for making the gene of claim 17 wherein the synthetic mutein has only one of said cysteine residues.

19. The method for making the gene of claim 17 wherein said cysteines of the synthetic mutein are substituted by serine, threonine, glycine, alanine, valine, leucine, isoleucine, histidine, tyrosine, phenylalanine, tryptophan or methionine.

20. The method of claim 17 or 18 wherein the mismatch defines a triplet that codes for serine or threonine.

21. The method of claim 17, 18 or 19 wherein the single-stranded DNA is a single-stranded phage that includes said strand and the mutational heteroduplex of step (b) is converted to closed circular heteroduplex.

22. The method of claim 17, 18 or 19 wherein said replicating is effected by transforming a competent bacterial host with the closed circular heteroduplex and culturing the resulting transformants.

* * * * *